United States Patent [19]
Strelchenko et al.

[11] Patent Number: 6,011,197
[45] Date of Patent: Jan. 4, 2000

[54] METHOD OF CLONING BOVINES USING REPROGRAMMED NON-EMBRYONIC BOVINE CELLS

[75] Inventors: Nikolai S. Strelchenko, DeForest; Jeffrey M. Betthauser, Windsor; Gail L. Jurgella, Madison; Marvin M. Pace, DeForest; Michael D. Bishop, Rio, all of Wis.

[73] Assignee: Infigen, Inc., Deforest, Wis.

[21] Appl. No.: 09/239,922

[22] Filed: Jan. 28, 1999

Related U.S. Application Data

[62] Continuation-in-part of application No. 08/812,851, Mar. 6, 1997, which is a continuation-in-part of application No. 08/812,031, filed as application No. PCT/US98/04345, Mar. 5, 1997

[60] Provisional application No. 60/073,019, Jan. 29, 1998.

[51] Int. Cl.$^7$ ................................................. C12N 15/00
[52] U.S. Cl. ................................ 800/24; 800/14; 800/15; 435/325
[58] Field of Search ................................ 800/24, 14, 15; 435/325

[56] References Cited

PUBLICATIONS

Abeydeera et al., "Coculture with follicular shell pieces can enhance the developmental competence of pig oocytes after in vitro fertilization: Relevance to Intracellular glutathione," *Biol. Reprod.* 58:213–218 (1998).

Ashworth et al, "DNA microsatellite analysis of Dolly," *Nature* 394:329 (1998).

Bellow et al., "Embryo transfer: Application of transvaginal ultrasound for performing amniocentesis in cattle," *Theriogenology* 45:225 (1996).

Bondioli et al., "Production of identical bovine offspring by nuclear transfer," *Theriogenology*, 33:165–174 (1990).

Bustad et al., "Miniature swine: Development, management and utilization," *Lab. Anim. Care* 18:280–287 (1986).

Campbell et al., "Sheep cloned by nuclear transfer from a cultured cell line," *Nature* 380:64–66 (1996).

Collas et al., "Nuclear transplantation by microinjection of inner cell mass and granulosa cell nuclei," *Mol. Reprod. Dev.* 38:264–267 (1994).

Damiani et al., "Evaluation of devlopmental competence, nuclear and ooplasmic maturation of calf oocytes," *Mol. Reprod. Dev.* 45:521–534 (1996).

Darling, *Animal Cells: Culture and Media* John Wiley & Sons, Ltd. p. 12 (1994).

Delhaise et al., "Nuclear transplantation using bovine primordial germ cells from male fetuses," *Reprod. Fert. Develop.* 7(5):1217–1219 (1995).

Dobrinsky et al., "Development of a culture medium (BECM-3) for porcine embryos: Effects of bovine serum albumin and fetal bovine serum on embryo development," *Biol. Reprod.* 55:1069–1074 (1996).

Donoghue et al., "Influence of gonadotropin treatment interval on follicular maturation, in vitro fertilization, circulating steroid concentrations, and subsequent luteal function in the domestic cat," *Biology Reprod.* 46:972–980 (1992).

Donoghue et al., "Timing of ovulation after gonadotrophin induction and its importance to successful intrauterine insemination in the tiger (Panthera tigris),"*J. Reprod. and Fertility* 107:53–58 (1996).

England et al., Conceptual and operational history of the development of miniature swine, *Swine in Biomedical Research* (M.E. Tubleson, ed.) Plenum Press, NY pp. 17–22 (1986).

Evans et al., "Derivation and preliminary characterization of pluripotent cell lines from porcine and bovine blastocysts," *Theriogenology* 33:125–129 (1990).

First et al., "Systems for production of calves from cultured bovine embyronic cells," *Reprod. Fertil. Dev.* 6:553–562 (1994).

Freshney, *Culture of Animal Cells: A Manual of Basic Technique*, 3rd Ed. 1994 (Table of Contents).

Funahashi et al., "Synchronization of meiosis in porcine oocytes by exposure to dibutyryl cyclic adenosine monophosphate improves development competence following in vitro fertilization," *Biol. Reprod.* 57:49–53 (1997).

Funahashi et al., "Effects of the duration of exposure to hormone supplements on cytoplasmic maturation of pig oocytes in vitro," *J. Reprod. Fert.* 98:179–185 (1993).

Funahashi et al., "Pronuclear formation and intracellular glutathione content of in vitro–matured porcine oocytes following in vitro fertilization and/or electrical activation," *Zygote* 3:273–281 (1995).

Funahashi et al., "Effects of electrical stimulation before or after in vitro fertilization on sperm penetration and pronuclear formation of pig oocytes," *Molecular Reproduction and Development* 36:361–367 (1993).

Garcia et al., "Bovine ultrasound–guided transvaginal amniocentesis," *Theriogenology* 47:1003–1008 (1997).

Geyer, "The role of insulator elements in defining domains of gene expression," *Curr. Opin. Genet. Dev.* 7:242–248 (1997).

Gillespie et al., *Hagan & Bruners Infectious Diseases of Domestic Animals*, 7$^{th}$ Ed., (1981).

Gordon, "Embryo transfer and associated techniques in pigs," *Controlled Reproduction in Pigs* pp. 164–182 (1997).

Goritz et al., *J. Reprod. and Fertility* 106:117–124 (1996).

Grocholova et al., "The protein phosphatase inhibitor okadaic acid inhibits exit from metaphase II in parthenogenetically activated pig oocytes," *J. Exp. Zoology* 277:49–56 (1997).

(List continued on next page.)

*Primary Examiner*—Deborah Crouch
*Attorney, Agent, or Firm*—Lyon & Lyon LLP

[57] ABSTRACT

The present invention relates to cloning technologies. The invention relates in part to immortalized and totipotent cells useful for cloning animals, the embryos produced from these cells using nuclear transfer techniques, animals that arise from these cells and embryos, and materials, methods, and processes for establishing such cells, embryos, and animals.

29 Claims, 4 Drawing Sheets

OTHER PUBLICATIONS

Hammer et al., "Production of transgenic rabbits, sheep and pigs by microinjection," *Nature* 315:680–685 (1985).

Hayflick et al., "Serial cultivation of human diploid cell strains," *Exp. Cell. Res.* 37:614–636 (1965).

Hayflick et al., "Serial cultivation of human diploid cell strains," *Exp. Cell. Res.* 25:585–621 (1961).

Hochereaude Reviers & Perreau, "In vitro culture of embryonic disc cells from porcine blastocysts," *Reprod. Nutr. Dev.* 33: 475–483.

Hoffert et al., "Transition from maternal to embryonic control of development in IVM/IVF domestic cat embryos," *Molecular Reprod. Dev.* 48:208–215 (1997).

Jewgenow, "Impact of peptide growth factors the culture of small preantral follicles of domestic cats," *Theriogenology* 45:889–895 (1996).

Johnston et al., "Influence of temperature and gas atmosphere on in–vitro fertilization and embryo development in domestic cats," *J. Reprod. Fert.* 92:377–382 (1991).

Jolliff et al., "Parthenogenic development of in vitro–matured, in vivo–cultured porcine oocytes beyond blastocyst," *Biology of Reproduction* 56:544–548 (1997).

Jollif et al., "Parthenogenic development of in vitro–matured porcine oocytes to blastocyst," *Biology of Reproduction* 50(Sup I):282 (1994).

Kato et al., "Chimerism of mouse male fetal germ cells at 15.5 days post coitum after nuclear transfer," *Journal of Reproduction and Fertility Abstract Series, Society for the Study of Fertility*, Annual Conference, Southampton 13:38 (1994).

Kojima, "Embryo transfer," *Manual of Pig Embryo Transfer Procedures* pp. 7–21 and 76–79 (1998).

Labosky et al., "Mouse embryonic germ (EG) cell lines: Transmission through the germline and differences in the methylation imprint of insulin–like growth factor 2 receptor (Igf2r) gene compared with embryonic stem (ES) cell lines," *Development* 120:3197–3204 (1994).

Lavoir et al., "Isolation and identification of germ cells from fetal bovine ovaries," *Molecular Reprod. Dev.* 37:413–424 (1994).

Leibo et al., "Prenatal diagnosis of sex in bovine fetuses by amniocentesis," *Theriogenology* 33:531–552 (1990).

Long et al., "Morphology and subsequent development in culture of bovine oocytes matured in vitro under various conditions of fertilization," *J. Reprod. Fert.* 102:361–369 (1994).

Luvoni et al., "Effect of medium–199 and fetal calf serum on in vitro maturation of domestic cat oocytes," J. Reprod. Fert. Suppl. 47:203–207 (1993).

Machaty et al., "Parthenogenetic activation of porcine oocytes with guanosine–5'–0–(3'–thiotriphosphate)[1]," *Biology of Reproduction* 52:753–758 (1995).

Machaty et al., "Activation of porcine oocytes via an exogenously introduced rat muscarinic M1 receptor," *Biology of Reproduction* 57:85–91 (1997).

Masui et al., "Cytoplasmic control of nuclear behavior during meiotic maturation of frog oocytes," *J. Exp. Zool.* 177:129–145 (1971).

Matsui et al., "Derivation of pluripotential embryonic stem cells from murine primordial germ cells in culture," *Cell* 70:841–847 (1992).

Matsui et al., "Effect of steel factor and leukemia inhibitory factor on murine primordial germ cells in culture," *Nature* 353:750–752 (1991).

Mattioli et al., "Changes in maturation–promoting activity in the cytoplasm of pig oocytes throughout maturation," *Molecular Reproduction and Development* 30:119–125 (1991).

Mattioli et al., "Developmental competence of pig oocytes matured and fertilized in vitro," *Theriogenology* 31:1201–1207 (1989).

McGrath et al., "Nuclear transplantatoin in the mouse embryo by microsurgery and cell fusion," *Science* 220:1300–1302 (1983).

Miller et al., "Expression of human or bovine growth hormone gene with a mouse metallothionein–1 promoter in transgenic swine alters the secretion of porcine growth hormone and insulin–like growth factor–I," *J. Endocrinology* 120:481–488 (1986).

*Molecular Cloning, A Laboratory Manual, 2$^{nd}$. Ed.*, 1989, Sambrook, Fritsch, and Maniatis, Cold Spring Harbor Laboratory Press (Table of Contents).

Moore et al., "The effects of human leukemia inhibitory factor (HLIF) and culture medium on in vitro differentiation of cultured porcine inner cell mass (PICM)," *In Vitro Cell Biol. Anim.* 33:62–71 (1997).

Moore et al., "Effect of heterologous hematopoietic cytokines on in vitro differentiation of cultured porcine inner cell masses," *Mol. Reprod. Dev.* 45:139–144 (1996).

Nagashima et al., "Transplantation of porcine blastomere nuclei into oocytes collected from prepubertal gilts," *J. Reprod. Dev.* 38:73–78 (1992).

Nagashima et al., "Nuclear transfer of porcine embryos using cryopreserved delipated blastomeres as donor nuclei," *Mol. Reprod. Dev.* 48:339–343 (1997).

Nichols et al., "Derivation of germline competent embryonic stem cells with a combination of interleukin–6 and soluble interleukin–6 and soluble interleukin–6 receptor," *Experimental Cell Research* 215:237–239 (1994).

Nurse, "Universal control mechanism regulating onset of M–phase," *Nature* 344:503–508 (1990).

Nussbaum et al., "Differential effects of protein synthesis inhibitors on porcine oocyte activation," *Molecular Reproduction and Development* 41:70–75 (1995).

Pennisi et al., "After Dolly, a pharming frenzy," *Science* 279:646–648 (1998).

Petters et al., "Culture of pig embryos," *J. Reprod. Fert.* (Suppl) 48:61–73 (1993).

Piedrahita et al., "Generation of transgenic porcine chimeras using primordial germ cell–derived colonies," *Biology of Reproduction* 58:1321–1329 (1989).

Piedrahita et al., "Advances in the generation of transgenic pigs via embryo–derived and primordial germ cell–derived cells," *J. Reprod. Fert.* (suppl) 52: 245–254 (1997).

Piedrahita et al., "On the isolation of embryonic stem cells: Comparative behavior of murine, porcine and ovine embryos," *Theriogenology* 34:879–901 (1990).

Pieterse et al., "Aspiration of bovine oocytes during transvaginal ultrasound scanning of the ovaries," *Theriogenology* 30:751–762 (1988).

Polge et al., "Embryo transplantation and preservation," *Control of Pig Reproduction* pp. 277–291.

Prather et al., "Nuclear transplantation in early pig embryos," *Biology of Reproduction* 41:414–418 (1989).

Prather et al., "Nuclear transplantation in the pig embryo: Nuclear swelling," *J. Exp. Zool.* 255:355–358 (1990).

Prather et al., "Artificial activation of porcine oocytes matured in vitro," *Molecular Reproduction and Development* 28:405–409 (1991).

Prochazka et al., "Development of pronuclei in pig oocytes activated by a single electric pulse," *J. Reprod. Fert.* 96:725–734 (1992).

Reed et al., "In vitro culture of pig embryos," *Theriogenology* 37: 95–109 (1992).

Resnick et al., "Long–term proliferation of mouse primordial germ cells in culture," *Nature* 359:550 (1992).

Rose–Hellkant et al., "Roles of protein kinase A and C in spontaneous maturation and in forskolin or 3–isobutyl–1–methylxanthine maintained meiotic arrest of bovine oocytes," *Mol. Reprod. Develop.* 44:241–249 (1996).

Rosekrans et al., "Effect of free amino acids and vitamins on cleavage and developmental rate of bovine zygotes in vitro," *J. Anim. Sci.* 72:434–437 (1994).

Roth et al., *Biology of Reprod.* 57:165–171 (1997).

Saito et al., "Ability of porcine blastomere nuclei derived from 8– and 16–cell stage embryos to support development following transfer to enucleated oocytes in vitro," *Assis. Reprod. Tech. Andro.* 259:257–266 (1992).

Saito et al., "Bovine embryonic stem cell–like cell lines cultured over several passages," *Roux's Arch Dev. Biol.* 201:134–141 (1992).

Salisbury et al., *Physiology of Reproduction and Artificial Insemination of Cattle*, $2^{nd}$ Ed. 1961 (Table of Contents).

Sawai et al., "Stage–specific requirement of cysteine during in vitro maturation of porcine oocytes for glutathione synthesis associated with male pronuclear formation," *Biol. Reprod.* 57: 1–6 (1997).

Schaeffer, "Terminology associated with cell, tissue and organ culture, molecular biology and molecular genetics," *In Vitro Cell Dev. Biol.* 26:97–101 (1990).

Schoenbeck et al., "Diacylglycerol–enhanced electrical activation of porcine oocytes matured in vitro," *Theriogenology* 40:257–266 (1993).

Seidel et al., *Embryo Transfer in Dairy Cattle*, W.D. Hoard & Sons, Co. 1989 (Table of Contents).

Seshagiri et al., "Phosphate is required for inhibition of glucose of development of hamster eight–cell embryos in vitro," *Biol. Reprod.* 40:607–614 (1989).

Shim et al., "Isolation of pluripotent stem cells from cultured porcine primordial germ cells," *Theriogenology* 47:245 (1997).

Signer et al., "DNA fingerprinting dolly," *Nature* 394:329 (1998).

Sims et al., "Production of calves by transfer of nuclei from cultured inner cell mass cells," *Proc. Natl. Acad. Sci. USA* 90:6143–6147 (1993).

Sims et al., "Production of fetuses from totipotent cultured bovine inner cell mass cells," *Theriogenology* 39:313 (1993).

Spector et al., *Cells: A Laboratory Manual vol. I: Culture and Biochemical analysis of cells*, Cold Spring Harbor Laboratory Press (1998).

Stice et al., "Multiple generational bovine embryo cloning," *Biology of Reproduction* 48:715–719 (1993).

Stice et al., "Pluripotent bovine embryonic cell lines direct embryonic development following nuclear transfer," *Biol. Reprod.* 54:100–110 (1996).

Strelchenko, "Bovine pluripotent stem cells," *Theriogenology* 45:131–140 (1996).

Strojek et al., "A method for cultivating morphologically undifferentiated embryonic stem cells form porcine blastocysts," *Theriogenology* 33:901–903 (1990).

Swanson et al., "Persistence of the developmental block of in vitro fertilized domestic cat embryos to temporal variations in culture conditions," *Molecular Reprod. Dev.* 43:298–305 (1996).

Terlouw et al., *Theriogenology* 37: 309 (1992).

*Transgenic Animals, Generation and Use*, Ed. L.M. Houdebine, Hardwood Academic Publishers: Australia (1997) (Table of Contents only).

Tsunoda et al., "Nuclear transplantation of embryonic stem cells in mice," *Journal of Reproduction and Fertility* 98(2):537–540 (1993).

Vos et al., "Bovine fetal fluid collection: Transvaginal, ultrasound–guided puncture technique," *Vet. Rec.* 127:502–504 (1990).

Wagoner et al., "Functional enucleation of bovine oocytes: Effects of centrifugation and ultraviolet light," *Theriogenology* 46:279–284 (1996).

Wakayama et al., "Full–term development of mice from enucleated oocytes injected with cumulus cell nuclei," *Nature* 394:369–374 (1998).

Wang et al., "Quantified analysis of cortical granule distribution and exocytosis of porcine oocytes during meiotic maturation and activation," *Biology of Reproduction* 56: 1376–1382 (1997).

Wells et al., "Production of cloned lambs from an established embryonic cell line: a comparison between in vivo– and in vitro–matured cytoplasts," *Biol. Repr.* 57:385–393 (1997).

Wheeler, "Development and validation of swine embryonic stem cells: A review," *Reprod. Fert. Dev.* 6:563–568 (1994).

Wianny et al., "Proliferation and differentiation of porcine inner cell mass and epiblast in vitro," *Biol. Reprod.* 57:756–764 (1997).

Willadsen, "Nuclear transplantation in sheep embryos," *Nature* 320:63–65 (1986).

Williams et al., "In vitro development of zygotes from prepubertal gilts after microinjection of DNA," *J. Ani. Sci.* 70:2207–2111 (1992).

Wilmut et al., "Viable offspring derived from fetal and adult mammalian cells," *Nature* 385:810–813 (1997).

Yang et al., "Micromanipulation of mammalian embryos: Principles, progress and future possibilities," *Theriogenology* 38:315–335 (1992).

Young et al., "Production of biopharmaceutical proteins in the milk of transgenic dairy animals," *BioPharm* 10(6):34–38 (1997).

METHOD OF CLONING BOVINES USING
REPROGRAMMED NON-EMBRYONIC
BOVINE CELLS

This application claims Priority from Provisional Application 60/073019, filed Jan. 29, 1998, which is a continuation in part of Ser. No. 08/812851, filed Mar. 6, 1997 and which is a continuation in part of Ser. No. 08/81 2031, filed Mar. 6, 1997; and which is a 371 of PCT/US98/04345, filed Mar. 5, 1998.

FIELD OF THE INVENTION

The invention relates to the cloning of animals.

BACKGROUND OF THE INVENTION

The following discussion of the background of the invention is merely provided to aid the reader in understanding the invention and is not admitted to describe or constitute prior art to the present invention.

Researchers have been developing methods for cloning mammalian animals over the past two decades. These reported methods typically include the steps of (1) isolating a cell, most often an embryonic cell; (2) inserting the cell or nucleus isolated from the cell into an enucleated oocyte (e.g., the oocyte's nucleus was previously extracted), and (3) allowing the embryo to mature in vivo.

The first successful nuclear transfer experiment using mammalian cells was reported in 1983, where the pronuclei isolated from a murine (mouse) zygote were inserted into an enucleated oocyte and resulted in like offspring(s). McGrath & Solter, 1983, *Science* 220:1300–1302. Subsequently, others described the production of chimeric murine embryos (e.g., embryos that contain a subset of cells having significantly different nuclear DNA from other cells in the embryo) using murine primordial germ cells (PGC). These cells are and can give rise to pluripotent cells (e.g., cells that can differentiate into other types of cells but do not differentiate into a grown animal). Matsui et al., 1992, *Cell* 70:841–847 and Resnick et al., 1992, *Nature* 359:550; Kato et al., 1994, *Journal of Reproduction and Fertility* Abstract Series, Society For the Study of Fertility, Annual Conference, Southampton, 13:38.

Some publications related to murine pluripotent cells stress the importance of steel factor for converting precursor cells into pluripotent cells. U.S. Pat. Nos. 5,453,357 and 5,670,372, entitled "Pluripotent Embryonic Stem Cells and Methods of Making Same," issued to Hogan. These same publications indicate that murine pluripotent cells exhibit strong, uniform alkaline phosphatase staining.

Although murine animals were never clearly cloned from nuclear transfer techniques using embryonic cells, some progress was reported in the field of cloning ovine (sheep) animals. One of the first successful nuclear transfer experiments utilizing ovine embryonic cells as nuclear donors was reported in 1986. Willadsen, 1986, *Nature* 320:63–65. A decade later, others reported that additional lambs were cloned from ovine embryonic cells. Campbell et al., 1996, *Nature* 380:64–66 and PCT Publication WO 95/20042. Recently, another lamb was reported to be cloned from ovine somatic mammary tissue. Wilmut et al., 1997, *Nature* 385:810–813. Some methods for cloning ovine animals focused upon utilizing serum deprived somatic ovine cells and cells isolated from ovine embryonic discs as nuclear donors. PCT Publications WO 96/07732 and WO 97/07669. Other methods for cloning ovine animals involved manipulating the activation state of an in vivo matured oocyte after nuclear transfer. PCT Publication WO 97/07668.

While few lambs were produced, publications that disclose cloned lambs report a cloning efficiency that is, at best, approximately 0.4%. Cloning efficiency, as calculated for the previous estimate, is a ratio equal to the number of cloned lambs divided by the number of nuclear transfers used to produce that number of cloned lambs.

Despite the slower progress endemic to the field of cloning bovine animals, a bovine animal was cloned using embryonic cells derived from 2–64 cell embryos. This bovine animal was cloned by utilizing the nuclear transfer techniques set forth in U.S. Pat. Nos. 4,994,384 and 5,057,420. Others reported that cloned bovine embryos were formed by nuclear transfer techniques utilizing the inner cell mass cells of a blastocyst stage embryo. Sims & First, 1993, *Theriogenology* 39:313 and Keefer et al., 1994, *Mol. Reprod. Dev.* 38:264–268. In addition, another publication reported that cloned bovine embryos were prepared by nuclear transfer techniques that utilized PGCs isolated from fetal tissue. Delhaise et al., 1995, *Reprod. Fert. Develop.* 7:1217–1219; Lavoir 1994, *J. Reprod. Dev.* 37:413–424; and PCT application WO 95/10599 entitled "Embryonic Stem Cell-Like Cells." However, the reports demonstrated that cloned PGC-derived bovine embryos never clearly developed past the first trimester during gestation. Similarly, embryonic stem cell (e.g., cell line derived from embryos which are undifferentiated, pluripotent, and can establish a permanent cell line which exhibits a stable karyotype), ESC, derived bovine embryos never developed past fifty-five days, presumably due to incomplete placental development. Stice et al., 1996, *Biol. Reprod.* 54: 100–110.

Despite the progress of cloning ovine and bovine animals, there remains a great need in the art for methods and materials that increase cloning efficiency. In addition there remains a great need in the art to expand the variety of cells that can be utilized as nuclear donors, especially expanding nuclear donors to non-embryonic cells. Furthermore, there remains a long felt need in the art for karyotypically stable permanent cell lines that can be used for genome manipulation and production of transgenic cloned animals.

SUMMARY

The present invention relates to cloning technologies. The invention relates in part to immortalized, totipotent cells useful for cloning animals, the embryos produced from these cells using nuclear transfer techniques, animals that arise from these cells and embryos, and the methods and processes for creating such cells, embryos, and animals.

The present invention provides multiple advantages over the tools and methods currently utilized in the field of mammalian cloning. Such features and advantages include:

(1) Production of cloned animals from virtually any type of cell. The invention provides materials and methods for reprogramming non-totipotent cells into totipotent cells. These non-totipotent cells may be of non-embryonic origin. This feature of the invention allows for the ability to assess the phenotype of an existing animal and then readily establish a permanent cell line for cloning that animal.

(2) Creation of permanent cell lines from virtually any type of cell. Permanent cell lines provide a nearly unlimited source of genetic material for nuclear transfer cloning techniques. In one aspect of the invention, non-totipotent precursor cells can be reprogrammed into totipotent and permanent cells. These non-totipotent precursor cells may be non-embryonic cells. Permanent cell lines provide the advantage of enhancing cloning efficiency due to the lower cellular heterogeneity within the cell lines (e.g., permanent cells that have lower rates of differentiation than primary culture cell lines currently used for cloning). In addition, the permanent cell lines can be manipulated in vitro to produce cells, embryos, and animals whose genomes have been manipulated (e.g., transgenic). Furthermore, permanent cell lines can be more easily stored, transported, and re-established in culture than other types of cell lines.

(3) Enhancement of the efficiency for cloning embryos as a result of utilizing asynchronous, permanent, and karyotypically stable cell lines in a complete in vitro embryo production system.

Cloning efficiency can be expressed by the ratio between the number of embryos resulting from nuclear transfer and the number of nuclear transfers performed to give rise to the embryos. Alternatively, cloning efficiency can be expressed as the ratio between the number of live born animals and the number of nuclear transfers performed to give rise to these animals.

Immortalized and Totipotent Cells of the Invention

In a first aspect, the invention features a totipotent mammalian cell. Preferably, the totipotent mammalian cell is (1) a cultured cell; (2) a cell cultured in a cell line; and (3) an immortalized cell. In addition, the mammalian cell is preferably an ungulate cell and more preferably a bovine cell.

The term "mammalian" or "mammal" as used herein refers to any animal of the class Mammalia. A mammalian animal of the invention is preferably an endangered animal, or, more preferably, a farm animal. Most preferably, a mammal is an ungulate.

The term "non-ovine" as used herein refers to any animal other than an animal of the family Ovidae. Members of the family Oviadae include sheep. A non-ovine mammal is any member of the class Mammalia other than an animal of the family Ovidae. Preferable non-ovine animals are ungulate animals and most preferably are bovine and porcine animals.

The term "ungulate" as used herein refers to a four-legged animal having hooves. In other preferred embodiments, the ungulate is selected from the group consisting of domestic or wild representatives of bovids, ovids, cervids, suids, equids and camelids. Examples of such representatives are cows or bulls, bison, buffalo, sheep, big-horn sheep, horses, ponies, donkeys, mule, deer, elk, caribou, goat, water buffalo, camels, llama, alpaca, and pigs. Especially preferred in the bovine species are *Bos taurus, Bos indicus*, and *Bos buffaloes* cows or bulls.

The term "bovine" as used herein refers to a family of ruminants belonging to the genus Bos or any closely related genera of the family Bovidae. The family Bovidae includes true antelopes, oxen, sheep, and goats, for example. Preferred bovine animals are the cow and ox. Especially preferred bovine species are *Bos taurus, Bos indicus*, and *Bos buffaloes*. Other preferred bovine species are *Bos primigenius and Bos longifrons*.

The term "totipotent" as used herein refers to a cell that gives rise to all of the cells in a developing cell mass, such as an embryo, fetus, and animal. In preferres embodiments, the term "totipotent" also refers to a cell that gives rise to all of the cells in an animal. A totipotent cell can give rise to all of the cells of a developing cell mass when it is utilized in a procedure for creating an embryo from one or more nuclear transfer steps. An animal may be an animal that functions ex utero. An animal can exist, for example, as a live born animal. Totipotent cells may also be used to generate incomplete animals such as those useful for organ harvesting, e.g., having genetic modifications to eliminate growth of a head such as by manipulation of a homeotic gene.

The terms "developing cell mass" as used herein refers to a group of cells in which all cells or a portion of the cells are undergoing cell division. The developing cell mass may be an embryo, a fetus, and/or an animal, for example. The developing cell mass may be dividing in vitro (e.g., in culture) or in vivo (e.g., in utero). The developing cell mass may be a product of one or more nuclear transfer processes or may be the product of oocyte activation (e.g., sperm mediated fertilization).

The term "live born" as used herein preferably refers to an animal that exists ex utero. A "live born" animal may be an animal that is alive for at least one second from the time it exits the maternal host. A "live born" animal may not require the circulatory system of an in utero environment for survival. A "live born" animal may be an ambulatory animal. Such animals can include pre- and post-pubescent animals. In addition, a "live born animal" may also be deceased for a certain period of time. As discussed previously, a "live born" animal may lack a portion of what exists in a normal animal of its kind. For example, a "live born" animal may lack a head as a result of the deletion or manipulation of one or more homeotic genes.

The term "totipotent" as used herein is to be distinguished from the term "pluripotent." The latter term refers to a cell that differentiates into a sub-population of cells within a developing cell mass, but is a cell that may not give rise to all of the cells in that developing cell mass. Thus, the term "pluripotent" can refer to a cell that cannot give rise to all of the cells in a live born animal.

The term "totipotent" as used herein is also to be distinguished from the term "chimer" or "chimera." The latter term refers to a developing cell mass that comprises a sub-group of cells harboring nuclear DNA with a significantly different nucleotide base sequence than the nuclear DNA of other cells in that cell mass. The developing cell mass can, for example, exist as an embryo, fetus, and/or animal.

The term "immortalized" or "permanent" as used herein in reference to cells refers to cells that have exceeded the Hayflick limit. The Hayflick limit can be defined as the number of cell divisions that occur before a cell line becomes senescent. Hayflick set this limit to approximately 60 divisions for most non-immortalized cells. See, e.g., Hayflick and Moorhead, 1961, *Exp. Cell. Res*. 25: 585–621; and Hayflick, 1965, *Exp. Cell Research* 37: 614–636, incorporated herein by reference in their entireties including all figures, tables, and drawings. Therefore, an immortalized cell line can be distinguished from non-immortalized cell lines if the cells in the cell line are able to undergo more than 60 divisions. If the cells of a cell line are able to undergo more than 60 cell divisions, the cell line is an immortalized or permanent cell line. The immortalized cells of the invention are preferably able to undergo more than 70 divisions, are more preferably able to undergo more than 80 divisions, and are most preferably able to undergo more than 90 cell divisions.

Typically, immortalized or permanent cells can be distinguished from non-immortalized and non-permanent cells on the basis that immortalized and permanent cells can be passaged at densities lower than those of non-immortalized cells. Specifically, immortalized cells can be grown to confluence (e.g., when a cell monolayer spreads across an entire plate) when plating conditions do not allow physical contact between the cells. Hence, immortalized cells can be distinguished from non-immortalized cells when cells are plated at cell densities where the cells do not physically contact one another.

The term "plated" or "plating" as used herein in reference to cells refers to establishing cell cultures in vitro. For example, cells can be diluted in cell culture media and then added to a cell culture plate or cell culture dish. Cell culture plates are commonly known to a person of ordinary skill in the art. Cells may be plated at a variety of concentrations and/or cell densities.

The meaning of the term "cell plating" can also extend to the term "cell passaging." Immortalized cells of the invention can be passaged using cell culture techniques well known to those skilled in the art. The term "cell passaging" can refer to such techniques which typically involve the steps of (1) releasing cells from a solid support and disassociation of these cells, and (2) diluting the cells in fresh media suitable for cell proliferation. Immortalized cells can be successfully grown by plating the cells in conditions where they lack cell to cell contact. Cell passaging may also refer to removing a portion of liquid medium bathing cultured cells and adding liquid medium from another source to the cell culture.

The term "proliferation" as used herein in reference to immortalized or permanent cells refers to a group of cells that can increase in size and/or can increase in numbers over a period of time.

The term "confluence" as used herein refers to a group of cells where a large percentage of the cells are physically contacted with at least one other cell in that group. Confluence may also be defined as a group of cells that grow to a maximum cell density in the conditions provided. For example, if a group of cells can proliferate in a monolayer and they are placed in a culture vessel in a suitable growth medium, they are confluent when the monolayer has spread across a significant surface area of the culture vessel. The surface area covered by the cells preferably represents about 50% of the total surface area, more preferably represents about 70% of the total surface area, and most preferably represents about 90% of the total surface area.

The term "culture" as used herein in reference to cells refers to one or more cells that are undergoing cell division or not undergoing cell division in an in vitro environment. An in vitro environment can be any medium known in the art that is suitable for maintaining cells in vitro, such as suitable liquid media or agar. Specific examples of suitable in vitro environments for cell cultures are described in *Culture of Animal Cells: a manual of basic techniques* (3$^{rd}$ edition), 1994, R. I. Freshney (ed.), Wiley-Liss, Inc.; *Cells: a laboratory manual* (vol. 1), 1998, D. L. Spector, R. D. Goldman, L. A. Leinwand (eds.), Cold Spring Harbor Laboratory Press; and *Animal Cells: culture and media*, 1994, D. C. Darling, S. J. Morgan, John Wiley and Sons, Ltd., each of which is incorporated herein by reference in its entirety including all figures, tables, and drawings. Preferred media are AminoMax™-C100 Basal Medium (Gibco 1701-082), AminoMax™ C-100 Supplement Medium (Gibco 17002-080), and KnockoUt™ D-MEM Medium (Gibco 10829-108).

Nearly any type of cell can be placed in cell culture conditions. Cells may be cultured in suspension and/or in monolayers with one or more substantially similar cells. Cells may be cultured in suspension and/or in monolayers with a heterogeneous population cells. The term "heterogeneous" as utilized in the previous sentence can relate to any cell characteristics, such as cell type and cell cycle stage, for example. Cells may be cultured in suspension and/or in monolayers with feeder cells. The term "feeder cells" is defined hereafter. In preferred embodiments, cells may be successfully cultured by plating the cells in conditions where they lack cell to cell contact. Cell cultures can also be utilized to establish a cell line.

In preferred embodiments, (1) cultured cells undergo cell division; (2) cells are cultured for greater than 5 hours; (3) cells are cultured for greater than 7 hours; (4) cells are cultured for greater than 10 hours; (5) cells are cultured for greater than 12 hours; (6) cells are cultured for greater than 24 hours; (7) cells are cultured for and greater than 48 hours; (8) cells are cultured greater than 3 days; (9) cells are cultured for greater than 5 days; (10) cells are cultured for greater than 10 days; and (11) cells are cultured for greater than 30 days.

The term "suspension" as used herein refers to cell culture conditions in which the cells are not attached to a solid support. Cells proliferating in suspension can be stirred while proliferating using apparatus well known to those skilled in the art.

The term "monolayer" as used herein refers to cells that are attached to a solid support while proliferating in suitable culture conditions. A small portion of the cells proliferating in the monolayer under suitable growth conditions may be attached to cells in the monolayer but not to the solid support. Preferably less than 15% of these cells are not attached to the solid support, more preferably less than 10% of these cells are not attached to the solid support, and most preferably less than 5% of these cells are not attached to the solid support. Cells can also grow in culture in multilayers. The term "multilayer" as used herein refers to cells proliferating in suitable culture conditions where at least 15% of the cells are indirectly attached to the solid support through an attachment to other cells. Preferably, at least 25% of the cells are indirectly attached to the solid support, more preferably at least 50% of the cells are indirectly attached to the solid support, and most preferably at least 75% of the cells are indirectly attached to the solid support.

The term "substantially similar" as used herein in reference to immortalized bovine cells refers to cells from the same organism and the same tissue. In preferred embodiments, substantially similar also refers to cell populations that have not significantly differentiated. For example, preferably less than 15% of the cells in a population of cells have differentiated, more preferably less than 10% of the cell population have differentiated, and most preferably less than 5% of the cell population have differentiated.

The term "cell line" as used herein refers to cultured cells that can be passaged more than once. The invention relates to cell lines that can be passaged more than 2, 5, 6, 7, 8, 9, 10, 15, 20, 30, 50, 80, 100, and 200 times, or preferably more than any integer between 2 and 200, each number not having been explicitly set forth in the interest of conciseness. The concept of cell passaging is defined previously.

In preferred embodiments, (1) the totipotent cells are not alkaline phosphatase positive; (2) the totipotent cells arise from at least one precursor cell; (3) the precursor cell is isolated from and/or arises from any region of an animal; (4) the precursor cell is isolated from and/or arises from any cell in culture; (5) the precursor cell is selected from the group consisting of a non-embryonic cell, a non-fetal cell, a differentiated cell, a somatic cell, an embryonic cell, a fetal cell, an embryonic stem cell, a primordial germ cell, a genital ridge cell, an amniotic cell, a fetal fibroblast cell, an ovarian follicular cell, a cumulus cell, an hepatic cell, an endocrine cell, an endothelial cell, an epidermal cell, an epithelial cell, a fibroblast cell, a hematopoletic cell, a keratinocyte, a renal cell, a lymphocyte, a melanocyte, a muscle cell, a myeloid cell, a neuronal cell, an osetoblast, a mesenchymal cell, a mesodermal cell, an adherent cell, a cell isolated from an asynchronous population of cells, and a cell isolated from a synchronized population of cells where the synchronous population is not arrested in the Go stage of the cell cycle; and (6) the precursor cell is preferably isolated and/or arises from a mammalian animal, more preferably an ungulate animal, and most preferably a bovine animal.

The term "alkaline phosphatasc positive" as used herein refers to a detectable presence of cellular alkaline phosphatase. Cells that are not alkaline phosphatase positive do not stain appreciably using a procedure for visualizing cellular alkaline phosphatase. Procedures for detecting the presence of cellular alkaline phosphatase are well-known to a person of ordinary skill in the art. See, e.g., Matsui et al., 1991, "Effect of Steel Factor and Leukemia Inhibitory Factor on Murine Primordial Germ Cells in Culture," *Nature* 353: 750–752. Examples of cells that stain appreciably for alkaline phosphatase can be found in the art. See, e.g., U.S. Pat. No. 5,453,357, Entitled "Pluripotent Embryonic Stem Cells and Methods of Making Same," issued to Hogan on Sep. 26, 1995, which is incorporated by reference herein in its entirety, including all figures, tables, and drawings.

The term "precursor cell" or "precursor cells" as used herein refers to a cell or cells used to create a cell line of totipotent cells. The cell line is preferably permanent. Precursor cells can be isolated from any mammal, preferably from an ungulate and more preferably from a bovine animal. The precursor cell or cells may be isolated from nearly any cellular entity. For example, a precursor cell or cells may be isolated from blastocysts, embryos, fetuses, and cell lines (e.g., cell lines established from embryonic cells), preferably isolated from fetuses and/or cell lines established from fetal cells, and more preferably isolated from ex utero animals and/or cell cultures and/or cell lines established from such ex utero animals. An ex utero animal may exist as a newborn animal, adolescent animal, yearling animal, and adult animal. The ex utero animals may be alive or post mortem. The precursor cell or cells may be immortalized or non-immortalized. These examples are not meant to be limiting and a further description of these exemplary precursor cells is provided hereafter.

The term "anrses from" as used herein refers to the conversion of one or more cells into one or more other cells. For example, a non-totipotent precursor cell can be converted into a totipotent cell by utilizing features of the invention described hereafter. This conversion process can be referred to as a reprogramming step. In another example, a precursor cell can give rise to a feeder layer of cells, as defined hereafter. In addition, the term "arises from" can refer to the creation of totipotent embryos from immortalized, totipotent cells of the invention, as described hereafter.

The term "reprogramming" or "reprogrammed" as used herein refers to materials and methods that can convert a non-totipotent cell into an totipotent cell. Distinguishing features between totipotent and non-totipotent cells are described previously. An example of materials and methods for converting non-totipotent cells into totipotent cells is to incubate precursor cells with a receptor ligand cocktail. Receptor ligand cocktails are described hereafter.

The term "isolated" as used herein refers to a cell that is mechanically separated from another group of cells. Examples of a group of cells are a developing cell mass, a cell culture, a cell line, and an animal. These examples are not meant to be limiting and the invention relates to any group of cells.

The term "non-embryonic cell" as used herein refers to a cell that is not isolated from an embryo. Non-embryonic cells can be differentiated or non-differentiated. Non-embryonic cells can refer to nearly any somatic cell, such as cells isolated from an ex utero animal. These examples are not meant to be limiting.

For the purposes of the present invention, the term "embryo" or "embryonic" as used herein refers to a developing cell mass that has not implanted into the uterine membrane of a maternal host. Hence, the term "embryo" as used herein can refer to a fertilized oocyte, a cybrid (defined herein), a pre-blastocyst stage developing cell mass, and/or any other developing cell mass that is at a stage of development prior to implantation into the uterine membrane of a maternal host. Embryos of the invention may not display a genital ridge. Hence, an "embryonic cell" is isolated from and/or has arisen from an embryo.

An embryo can represent multiple stages of cell development. For example, a one cell embryo can be referred to as a zygote, a solid spherical mass of cells resulting from a cleaved embryo can be referred to as a morula, and an embryo having a blastocoel can be referred to as a blastocyst.

The term "fetus" as used herein refers to a developing cell mass that has implanted into the uterine membrane of a maternal host. A fetus can include such defining features as a genital ridge, for example. A genital ridge is a feature easily identified by a person of ordinary skill in the art, and is a recognizable feature in fetuses of most animal species. The term "fetal cell" as used herein can refer to any cell isolated from and/or has arisen from a fetus or derived from a fetus. The term "non-fetal cell" is a cell that is not derived or isolated from a fetus.

The term "primordial germ cell" as used herein refers to a diploid somatic cell capable of becoming a germ cell. Primordial germ cells can be isolated from the genital ridge of a developing cell mass. The genital ridge is a section of a developing cell mass that is well-known to a person of ordinary skill in the art. See, e.g., Strelchenko, 1996, *Theriogenology* 45: 130–141 and Lavoir 1994, *J. Reprod. Dev.* 37: 413–424.

The terms "embryonic germ cell" and "EG cell" as used herein refers to a cultured cell that has a distinct flattened morphology and can grow within monolayers in culture. An EG cell may be distinct from a fibroblast cell. This EG cell morphology is to be contrasted with cells that have a spherical morphology and form multicellular clumps on feeder layers. Embryonic germ cells may not require the presence of feeder layers or presence of growth factors in cell culture conditions. Embryonic germ cells may also grow with decreased doubling rates when these cells approach confluence on culture plates. Embryonic germ cells of the invention may be totipotent. Embryonic germ cells of the invention may not appreciably stain for alkaline phosphatase. Preferably, embryonic germ cells are established in culture media that contains a significant concentration of glucose.

Embryonic germ cells may be established from a cell culture of nearly any type of precursor cell. Examples of precursor cells are discussed herein, and a preferred precursor cell for establishing an embryonic germ cell culture is a genital ridge cell from a fetus. Genital ridge cells are preferably isolated from porcine fetuses where the fetus is between 20 days and parturition, between 30 days and 100 days, more preferably between 35 days and 70 days and between 40 days and 60 days, and most preferably about a 55 day fetus. An age of a fetus can be determined as described above. The term "about" with respect to fetuses can refer to plus or minus five days. As described herein, EG cells may be physically isolated from a primary culture of cells, and these isolated EG cells may be utilized to establish a cell culture that eventually forms a homogenous or nearly homogenous line of EG cells.

The term "embryonic stem cell" as used herein refers to pluripotent cells isolated from an embryo that are maintained in in vitro cell culture. Embryonic stem cells may be cultured with or without feeder cells. Embryonic stem cells can be established from embryonic cells isolated from embryos at any stage of development, including blastocyst stage embryos and pre-blastocyst stage embryos. Embryonic stem cells are well known to a person of ordinary skill in the art. See, e.g., WO 97/37009, entitled "Cultured Inner Cell Mass Cell-Lines Derived from Ungulate Embryos," Stice and Golueke, published Oct. 9, 1997, and Yang & Anderson, 1992, *Theriogenology* 38: 315–335, both of which are incorporated herein by reference in their entireties, including all figures, tables, and drawings.

The term "amniotic cell" as used herein refers to any cultured or non-cultured cell isolated from amniotic fluid. Examples of methods for isolating and culturing amniotic cells are discussed in Bellow el al., 1996, *Theriogenology* 45: 225; Garcia & Salaheddine, 1997, *Theriogenology* 47: 1003–1008; Leibo & Rail, 1990, *Theriogenology* 33: 531–552; and Vos et al., 1990, *Vet. Rec.* 127: 502–504, each of which is incorporated herein by reference in its entirety, including all figures tables and drawings. Particularly preferred are cultured amniotic cells that are spherical (e.g., cultured amniotic cells that do not display a fibroblast-like morphology). Also preferred amniotic cells are fetal fibroblast cells. The terms "fibroblast," "fibroblast-like," "fetal," and "fetal fibroblast" are defined hereafter.

The terms "fibroblast-like" and "fibroblast" as used herein refer to cultured cells that have a distinct flattened morphology and that are able to grow within monolayers in culture.

The term "fetal fibroblast cell" as used herein refers to any differentiated fetal cell having a fibroblast appearance. While fibroblasts characteristically have a flattened appearance when cultured on culture media plates, fetal fibroblast cells can also have a spindle-like morphology. Fetal fibroblasts may require density limitation for growth, may generate type I collagen, and may have a finite life span in culture of approximately fifty generations. Preferably, fetal fibroblast cells rigidly maintain a diploid chromosomal content. For a description of fibroblast cells, see, e.g., *Culture of Animal Cells: a manual of basic techniques* (3$^{rd}$ edition), 1994, R. I. Freshney (ed), Wiley-Liss, Inc., incorporated herein by reference in its entirety, including all figures, tables, and drawings.

The terms "morphology" and "cell morphology" as used herein refer to form, structure, and physical characteristics of cells. For example, one cell morphology is significant levels of alkaline phosphatase, and this cell morphology can be identified by determining whether a cell stains appreciably for alkaline phosphatase. Another example of a cell morphology is whether a cell is flat or round in appearance when cultured on a surface or in the presence of a layer of feeder cells. Many other cell morphologies are known to a person of ordinary skill in the art and are cell morphologies are readily identifiable using materials and methods well known to those skilled in the art. See, e.g., Culture of Animal Cells: a manual of basic techniques (3$^{rd}$ edition), 1994, R. I. Freshney (ed.), Wiley-Liss, Inc.

The term "ovarian follicular cell" as used herein refers to a cultured or non-cultured cell obtained from an ovarian follicle, other than an oocyte. Follicular cells may be isolated from ovarian follicles at any stage of development, including primordial follicles, primary follicles, secondary follicles, growing follicles, vesicular follicles, maturing follicles, mature follicles, and graafian follicles. Furthermore, follicular cells may be isolated when an oocyte in an ovarian follicle is immature (i.e., an oocyte that has not progressed to metaphase II) or when an oocyte in an ovarian follicle is mature (i.e., an oocyte that has progressed to metaphase II or a later stage of development). Preferred follicular cells include, but are not limited to, pregranulosa cells, granulosa cells, theca cells, columnar cells, stroma cells, theca interna cells, theca externa cells, mural granulosa cells, luteal cells, and corona radiata cells. Particularly preferred follicular cells are cumulus cells. Various types of follicular cells are known and can be readily distinguished by those skilled in the art. See, e.g., *Laboratory Production of Cattle Embryos*, 1994, Ian Gordon, CAB International; *Anatomy and Physiology of Farm Animals* (5th ed.), 1992, R. D. Frandson and T. L. Spurgeon, Lea & Febiger, each of which is incorporated herein by reference in its entirety including all figures, drawings, and tables. Individual types of follicular cells may be cultured separately, or a mixture of types may be cultured together.

The term "cumulus cell" as used herein refers to any cultured or non-cultured cell isolated from cells and/or tissue surrounding an oocyte. Persons skilled in the art can readily identify cumulus cells. Examples of methods for isolating and/or culturing cumulus cells are discussed in Damiani et al., 1996, *Mol. Reprod. Dev.* 45: 521–534; Long et al., 1994, *J Reprod. Fert.* 102: 361–369; and Wakayama et al., 1998, *Nature* 394: 369–373, each of which is incorporated herein by reference in its entireties, including all figures, tables, and drawings. Cumulus cells may be isolated from ovarian follicles at any stage of development, including primordial follicles, primary follicles, secondary follicles, growing follicles, vesicular follicles, maturing follicles, mature follicles, and graafian follicles. Cumulus cells may be isolated from oocytes in a number of manners well known to a person of ordinary skill in the art. For example, cumulus cells can be separated from oocytes by pipeting the cumulus cell/oocyte complex through a small bore pipette, by exposure to hyaluronidase, or by mechanically disrupting (e.g. vortexing) the cumulus cell/oocyte complex. Additionally, exposure to $Ca^{++}/Mg^{++}$ free media can remove cumulus from immature oocytes. Also, cumulus cell cultures can be established by placing imatured oocytes in cell culture media. Once cumulus cells are removed from media containing increased LH/FSH concentrations, they can to attach to the culture plate.

The term "hepatic cell" as used herein refers to any cultured or non-cultured cell isolated from a liver. Particularly preferred hepatic cells include, but are not limited to, a hepatic parenchymal cell, a Kuipffer cell, an Ito cell, a hepatocyte, a fat-storing cell, a pit cell, and a hepatic endothelial cell. Persons skilled in the art can readily identify the various types of hepatic cells. See, e.g., *Regulation of Hepatic Metabolism*, 1986, Thurman et al. (eds.), Plenum Press, which is incorporated herein by reference in its entirety including all figures, drawings, and tables.

The term "differentiated cell" as used herein refers to a precursor cell that has developed from an unspecialized phenotype to that of a specialized phenotype. For example, embryonic cells can differentiate into an epithelial cell lining the intestine. It is highly unlikely that differentiated cells revert into their precursor cells in vivo or in vitro. However, materials and methods of the invention can reprogram differentiated cells into immortalized, totipotent cells. Differentiated cells can be isolated from a fetus or a live born animal, for example.

In contrast to the totipotent and/or immortalized cells of the invention that arise from non-embryonic cells, an example of embryonic cells is discussed in WO 96/07732, entitled "Totipotent Cells for Nuclear Transfer," hereby incorporated herein by reference in its entirety including all figures, drawings, and tables. The WO 96/07732 publication relates primarily to ovine animals. A unique feature of the present invention is that immortalized, totipotent cells are reprogrammed from non-embryonic cells by utilizing the materials and methods described herein in descriptions of the preferred embodiments and exemplary embodiments.

The term "asynchronous population" as used herein refers to cells that are not arrested at any one stage of the cell cycle. Many cells can progress through the cell cycle and do not arrest at any one stage, while some cells can become arrested at one stage of the cell cycle for a period of time. Some known stages of the cell cycle are $G_0$, $G_1$, S, $G_2$, and M. An asynchronous population of cells is not manipulated to synchronize into any one or predominantly into any one of these phases. Cells can be arrested in the $G_0$ stage of the cell cycle, for example, by utilizing multiple techniques known in the art, such as by serum deprivation. Examples of methods for arresting non-immortalized cells in one part of the cell cycle are discussed in WO 97/07669, entitled "Quiescent Cell Populations for Nuclear Transfer," hereby incorporated herein by reference in its entirety, including all figures, tables, and drawings.

The terms "synchronous population" and "synchronizing" as used herein refer to a fraction of cells in a population that are arrested (i.e., the cells are not dividing) in a discreet stage of the cell cycle. Synchronizing a population of cells, by techniques such as serum deprivation, may render the cells quiescent. The term "quiescent" is defined below. Preferably, about 50% of the cells in a population of cells are arrested in one stage of the cell cycle, more preferably about 70% of the cells in a population of cells are arrested in one stage of the cell cycle, and most preferably about 90% of the cells in a population of cells are arrested in one stage of the cell cycle. Cell cycle stage can be distinguished by relative cell size as well as by a variety of cell markers well known to a person of ordinary skill in the art. For example, cells can be distinguished by such markers by using flow cytometry techniques well known to a person of ordinary skill in the art. Alternatively, cells can be distinguished by size utilizing techniques well known to a person of ordinary skill in the art, such as by the utilization of a light microscope and a micrometer, for example.

The terms "serum deprivation," "serum starved," and "serum starvation" as used herein refer to culturing cells in a medium comprising a serum concentration sufficiently low as to render cultured cells quiescent. The term "quiescent" is defined hereafter. A number of sera are used by those skilled in the art to supplement cell culture media. Particularly preferred is fetal bovine serum. Preferred serum starvation conditions are culturing cells in a medium comprising less than 1% fetal bovine serum. Particularly preferred conditions are culturing cells in a medium comprising not more than 0.5% fetal bovine serum. A length of time cultured cells are serum starved to be rendered quiescent can vary depending upon cell type. Cultured cells can be serum starved for at least 1 hour, at least 5 hours, at least 12 hours, and at least 24 hours. Preferably, cultured cells are serum starved for more than 1 day. Most preferably, cultured cells are serum starved for more than 3 days. These conditions are not meant to be limiting, and other serum starvation conditions can easily be identified by those skilled in the art without undue experimentation.

The term "quiescent" as used herein in reference to cells refers to cells which are not dividing. A "quiescent cell culture" refers to a culture in which a majority of cells in the culture are not dividing. More preferably, in a quiescent cell culture all cells in the culture are not dividing. As discussed herein, a cell culture may be rendered quiescent by serum starvation, but other methods which render cell cultures quiescent are known to those of ordinary skill in the art. Cells may be made permanently quiescent, and more preferably, quiescent cells may be made to resume dividing at a later time.

In preferred embodiments, (1) the totipotent cells of the invention comprise modified nuclear DNA; (2) the modified nuclear DNA includes a DNA sequence that encodes a recombinant product; (3) the recombinant product is a polypeptide; (4) the recombinant product is a ribozyme; (4) the recombinant product is expressed in a biological fluid or tissue; (5) the recombinant product confers or partially confers resistance to one or more diseases; (6) the recombinant product confers resistance or partially confers resistance to one or more parasites; (7) the modified nuclear DNA comprises at least one other DNA sequence that can function as a regulatory element; (8) the regulatory element is selected from the group consisting of promotor, enhancer, insulator, and repressor; and (9) the regulatory clement is selected from the group consisting of milk protein promoter, urine protein promoter, blood protein promoter, tear duct protein promoter, synovial protein promoter, mandibular gland protein promoter, casein promoter, β-casein promoter, melanocortin promoter, milk serum protein promoter, (α-lactalbumin promoter, whey acid protein promoter, uroplakin promoter, (α-actin promoter.

The term "modified nuclear DNA" as used herein refers to the nuclear deoxyribonucleic acid sequence of a cell, embryo, fetus, or animal of the invention that has been manipulated by one or more recombinant DNA techniques. Examples of these recombinant DNA techniques are well known to a person of ordinary skill in the art, which can include (1) inserting a DNA sequence from another organism (e.g., a human organism) into target nuclear DNA, (2) deleting one or more DNA sequences from target nuclear DNA, and (3) introducing one or more base mutations (e.g., site-directed mutations) into target nuclear DNA. Cells with modified nuclear DNA can be referred to as "transgenic cells" for the purposes of the invention. Transgenic cells can be useful as materials for nuclear transfer cloning techniques provided herein.

Methods and tools for insertion, deletion, and mutation of nuclear DNA of mammalian cells are well-known to a person of ordinary skill in the art. See, *Molecular Cloning, a Laboratory Manual*, 2nd Ed., 1989, Sambrook, Fritsch, and Maniatis, Cold Spring Harbor Laboratory Press; U.S. Pat. No. 5,633,067, "Method of Producing a Transgenic Bovine or Transgenic Bovine Embryo," DeBoer et al., issued May 27, 1997; U.S. Pat. No. 5,612,205, "Homologous Recombination in Mammalian Cells," Kay et al., issued Mar. 18, 1997; and PCT publication WO 93/22432, "Method for Identifying Transgenic Pre-Implantation Embryos," all of which are incorporated by reference herein in their entirety, including all figures, drawings, and tables. These methods include techniques for transfecting cells with foreign DNA fragments and the proper design of the foreign DNA fragments such that they effect insertion, deletion, and/or mutation of the target DNA genome.

Transgenic cells may be obtained in a variety of manners. For example, transgenic cells can be isolated from a transgenic animal. Examples of transgenic animals are well known in the art, as described herein with regard to transgenic bovine and ovine animals. Cells isolated from a transgenic animal can be converted into totipotent and/or immortalized cells by using the materials and methods provided herein. In another example, transgenic cells can be created from totipotent and/or immortalized cells of the invention. Materials and methods for converting non-transgenic cells into transgenic cells are well known in the art, as described previously.

Any of the cell types defined herein can be altered to harbor modified nuclear DNA. For example, embryonic stem cells, fetal cells, and any totipotent and immortalized cell defined herein can be altered to harbor modified nuclear DNA.

Examples of methods for modifying a target DNA genome by insertion, deletion, and/or mutation are retroviral insertion, artificial chromosome techniques, gene insertion, random insertion with tissue specific promoters, homologous recombination, gene targeting, transposable elements, and/or any other method for introducing foreign DNA. Other modification techniques well known to a person of ordinary skill in the art include deleting DNA sequences from a genome, and/or altering nuclear DNA sequences. Examples of techniques for altering nuclear DNA sequences are site-directed mutagenesis and polymerase chain reaction procedures. Therefore, the invention provides for bovine cells that are simultaneously totipotent, immortalized, and transgenic. These transgenic, totipotent, immortalized cells can serve as nearly unlimited sources of donor cells for production of cloned transgenic animals.

The term "recombinant product" as used herein refers to the product produced from a DNA sequence that comprises at least a portion of the modified nuclear DNA. This product can be a peptide, a polypeptide, a protein, an enzyme, an antibody, an antibody fragment, a polypeptide that binds to a regulatory element (a term described hereafter), a structural protein, an RNA molecule, and/or a ribozyme, for example. These products are well defined in the art. This list of products is for illustrative purposes only and the invention relates to other types of products.

The term "ribozyme" as used herein refers to ribonucleic acid molecules that can cleave other RNA molecules in specific regions. Ribozymes can bind to discrete regions on a RNA molecule, and then specifically cleave a region within that binding region or adjacent to the binding region. Ribozyme techniques can thereby decrease the amount of polypeptide translated from formerly intact message RNA molecules. For specific descriptions of ribozymes, see U.S. Pat. No. 5,354,855, entitled "RNA Ribozyme which Cleaves Substrate RNA without Formation of a Covalent Bond," Cech et al., issued on Oct. 11, 1994, and U.S. Pat. No, 5,591,610, entitled "RNA Ribozyme Polymerases, Dephosphorylases, Restriction Endoribonucleases and Methods," Cech et al., issued on Jan. 7, 1997, both of which are incorporated by reference in their entireties including all figures, tables, and drawings.

The term "biological fluid or tissue" as used herein refers to any fluid or tissue in a biological organism. The fluids may include, but are not limited to, tears, saliva, milk, urine, amniotic fluid, semen, plasma, oviductal fluid, and synovial fluid. The tissues may include, but are not limited to, lung, heart, blood, liver, muscle, brain, pancreas, skin, and others.

The term "confers resistance" as used herein refers to the ability of a recombinant product to completely abrogate or partially alleviate the symptoms of a disease or parasitic condition. Hence, if the disease is related to inflammation, for example, a recombinant product can confer resistance to that inflammation if the inflammation decreases upon expression of the recombinant product. A recombinant product may confer resistance or partially confer resistance to a disease or parasitic condition, for example, if the recombinant product is an anti-sense RNA molecule that specifically binds to an mRNA molecule encoding a polypeptide responsible for the inflammation. Other examples of conferring resistance to diseases or parasites are described hereafter. In addition, examples of diseases are described hereafter.

Examples of parasites and strategies for conferring resistance to these parasites are described hereafter. These examples include, but are not limited to, worms, insects, invertebrate, bacterial, viral, and eukaryotic parasites. These parasites can lead to diseased states that can be controlled by the materials and methods of the invention.

The term "regulatory element" as used herein refers to a DNA sequence that can increase or decrease the amount of product produced from another DNA sequence. The regulatory element can cause the constitutive production of the product (e.g., the product can be expressed constantly). Alternatively, the regulatory element can enhance or diminish the production of a recombinant product in an inducible fashion (e.g., the product can be expressed in response to a specific signal). The regulatory element can be controlled, for example, by nutrition, by light, or by adding a substance to the transgenic organism's system. Examples of regulatory elements well-known to those of ordinary skill in the art are promoters, enhancers, insulators, and repressors. See, e.g., *Transgenic Animals, Generation and Use*, 1997, Edited by L. M. Houdebine, Hardwood Academic Publishers, Australia, hereby incorporated herein by reference in its entirety including all figures, tables, and drawings.

The term "promoters" or "promoter" as used herein refers to a DNA sequence that is located adjacent to a DNA sequence that encodes a recombinant product. A promoter is preferably operatively linked to the adjacent DNA sequence. A promoter typically increases the amount of recombinant product expressed from a DNA sequence as compared to the amount of the expressed recombinant product when no promoter exists. A promoter from one organism can be utilized to enhance recombinant product expression from a DNA sequence that originates from another organism. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art. Examples of promoter elements are described hereafter.

The term "enhancers" or "enhancer" as used herein refers to a DNA sequence that is located adjacent to the DNA sequence that encodes a recombinant product. Enhancer elements are typically located upstream of a promoter element or can be located downstream of the coding DNA sequence (e.g., the DNA sequence transcribed or translated into a recombinant product or products). Hence, an enhancer element can be located 100 base pairs, 200 base pairs, or 300 or more base pairs upstream of the DNA sequence that encodes the recombinant product. Enhancer elements can increase the amount of recombinant product expressed from a DNA sequence above the increased expression afforded by a promoter element. Multiple enhancer elements are readily available to persons of ordinary skill in the art.

The term "insulators" or "insulator" as used herein refers to DNA sequences that flank the DNA sequence encoding the recombinant product. Insulator elements can direct the recombinant product expression to specific tissues in an organism. Multiple insulator elements are well known to persons of ordinary skill in the art. See, e.g., Geyer, 1997, *Curr. Opin. Genet. Dev.* 7: 242–248, hereby incorporated herein by reference in its entirety, including all figures, tables, and drawings.

The term "repressor" or "repressor element" as used herein refers to a DNA sequence located in proximity to the DNA sequence that encodes the recombinant product, where the repressor sequence can decrease the amount of recombinant product expressed from that DNA sequence. Repressor elements can be controlled by the binding of a specific molecule or specific molecules to the repressor element DNA sequence. These molecules can either activate or deactivate the repressor element. Multiple repressor elements are available to a person of ordinary skill in the art.

The terms "milk protein promoter," "urine protein promoter," "blood protein promoter," "tear duct protein promoter," "synovial protein promoter," and "mandibular gland protein promoter" refer to promoter elements that regulate the specific expression of proteins within the specified fluid or gland or cell type in an animal. For example, a milk protein promoter is a regulatory element that can control the expression of a protein that is expressed in the milk of an animal. Other promoters, such as casein promoter, α-lactalbumin promoter, whey acid protein promoter, uroplakin promoter, and α-actin promoter, for example, are well known to a person of ordinary skill in the art.

In preferred embodiments, (1) the totipotent cell is subject to manipulation; (2) the manipulation comprises the step of utilizing a totipotent cell in a nuclear transfer procedure; (3) the manipulation comprises the step of cryopreserving the totipotent cells; (4) the manipulation comprises the step of thawing the totipotent cells; (5) the manipulation comprises the step of passaging totipotent cells; (6) the manipulation comprises the step of synchronizing totipotent cells; (7) the manipulation comprises the step of transfecting totipotent cells with foreign DNA; and (8) the manipulation comprises the step of dissociating a cell from another cell or group of cells.

The term "manipulation" as used herein refers to the common usage of the term, which is the management or handling directed towards some object. Examples of manipulations are described herein.

The term "nuclear transfer" as used herein refers to introducing a full complement of nuclear DNA from one cell to an enucleated cell. Nuclear transfer methods are well known to a person of ordinary skill in the art. See, U.S. Pat. No. 4,994,384, entitled "Multiplying Bovine Embryos," Prather et al., issued on Feb. 19, 1991 and U.S. Pat. No. 5,057,420, entitled "Bovine Nuclear Transplantation," Massey, issued on Oct. 15, 1991, both of which are hereby incorporated by reference in their entirety including all figures, tables and drawings. Nuclear transfer may be accomplished by using oocytes that are not surrounded by a zona pellucida.

Although the basic principals of nuclear transfer have been described previously, the technique can be sensitive to the introduction of any new parameters. Therefore, significant modifications to the techniques described in the area of nuclear transfer may require some experimentation to determine the practical effect of these modifications upon the efficiency of nuclear transfer. An example of a variable that can affect nuclear transfer efficiency is the age of the oocyte utilized for enucleation and nuclear transfer.

The term "cryopreserving" as used herein refers to freezing a cell, embryo, or animal of the invention. The cells, embryos, or portions of animals of the invention are frozen at temperatures preferably lower than 0° C., more preferably lower than −80° C., and most preferably at temperatures lower than −196° C. Cells and embryos in the invention can be cryopreserved for an indefinite amount of time. It is known that biological materials can be cryopreserved for more than fifty years. For example, semen that is cryopreserved for more than fifty years can be utilized to artificially inseminate a female bovine animal. Methods and tools for cryopreservation are well-known to those skilled in the art. See, e.g., U.S. Pat. No. 5,160,312, entitled "Cryopreservation Process for Direct Transfer of Embryos," issued to Voelkel on Nov. 3, 1992.

The term "thawing" as used herein refers to the process of increasing the temperature of a cryopreserved cell, embryo, or portions of animals. Methods of thawing cryopreserved materials such that they are active after the thawing process are well-known to those of ordinary skill in the art.

The terms "transfected," "transformation," and "transfection" as used herein refer to methods of inserting foreign DNA into a cellular organism. These methods involve a variety of techniques, such as treating the cells with high concentrations of salt, an electric field, liposomes, polycationic micelles, or detergent, to render the host cell outer membrane or wall permeable to nucleic acid molecules of interest. Transfection techniques are well known to a person of ordinary skill in the art and materials and methods for carrying out transfection of DNA constructs into cells are commercially available. Materials typically used to transfect cells with DNA constructs are lipophilic compounds such as Lipofectin™. Particular lipophilic compounds can be induced to form liposomes for mediating transfection of the DNA construct into the cells. These specified methods are not limiting and the invention relates to any transformation technique well known to a person of ordinary skill in the art. See, e.g., *Molecular Cloning, a Laboratory Manual*, 2nd Ed., 1989, Sambrook, Fritsch, and Maniatis, Cold Spring Harbor Laboratory Press and *Transgenic Animnals, Generation and Use*, 1997, Edited by L. M. Houdebine, Hardwood Academic Publishers, Australia, both of which were previously incorporated by reference.

The term "foreign DNA" as used herein refers to DNA that can be transfected into a target cell, where the foreign DNA harbors at least one base pair modification as compared to the nuclear DNA of the target organism. Foreign DNA and transfection can be further understood and defined in conjunction with the term "modified nuclear DNA," described previously.

The term "dissociating" as used herein refers to the materials and methods useful for pulling a cell away from another cell. For example, a blastomere (i.e., a cellular member of a blastocyst stage embryo) can be pulled away from the rest of the developing cell mass by techniques and apparatus well known to a person of ordinary skill in the art. See, e.g., U.S. Pat. No. 4,994,384, entitled "Multiplying Bovine Embryos," issued on Feb. 19, 1991, hereby incorporated herein by reference in its entirety, including all figures, tables, and drawings. Alternatively, cells proliferating in culture can be separated from one another to facilitate such processes as cell passaging, which is described previously. In addition, dissociation of a cultured cell from a group of cultured cells can be useful as a first step in the process of nuclear transfer, as described hereafter. When a cell is dissociated from an embryo, the dissociation manipulation can be useful for such processes as re-cloning, a process described herein, as well as a step for multiplying the number of embryos.

In another aspect, the invention features a totipotent mammalian cell, where the cell is immortalized, prepared by a process comprising the steps of: (a) isolating at least one precursor cell; and (b) introducing a stimulus to the precursor cell that converts the precursor cell into the totipotent mammalian cell.

The term "converts" as used herein refers to the phenomenon in which precursor cells become immortalized and/or totipotent. The term "convert" is synonymous with the term "reprogram" as used herein when the precursor cell is non-immortalized and/or non-totipotent. Precursor cells can be converted into totipotent, immortalized cells in varying proportions. For example, it is possible that only a small portion of precursor cells are converted into totipotent, immortalized cells. In the art, some researchers have discussed techniques for converting precursor cells into pluripotent cells. Matsui et al., 1992, *Cell* 70: 841–847.

The term "stimulus" as used herein refers to materials and/or methods useful for converting precursor cells into immortalized and/or totipotent cells. The stimulus can be electrical, mechanical, temperature-related, and/or chemical, for example. The stimulus may be a combination of one or more different types of stimuli. As described herein in exemplary embodiments, placing precursor cells in culture can be a sufficient stimulus to convert precursor cells into immortalized and/or totipotent cells. A stimulus can be introduced to precursor cells for any period of time that accomplishes the conversion of precursor cells into immortalized and/or totipotent cells.

The term "introduce" as used herein in reference to a stimulus refers to a step or steps in which precursor cells are contacted with a stimulus. If the stimulus is chemical in nature, for example, the stimulus may be introduced to the precursor cells by mixing the stimulus with cell culture medium.

In preferred embodiments (1) the precursor cells are co-cultured with feeder cells; (2) the precursor cells are not co-cultured with feeder cells; (3) the feeder cells are established from fetal cells; (4) the fetal cells arise from a fetus where no cell types have been removed from the fetus; (5) the fetal cells arise from a fetus where one or more cell types have been removed from the fetus; (6) the stimulus is introduced to precursor cells by feeder cells; (7) the feeder cells are the only source of the stimulus; (8) the stimulus is introduced to the precursor cells in a mechanical fashion; (9) the only stimulus is introduced to the precursor cells in a mechanical fashion; (10) the stimulus is introduced to the precursor cells by feeder cells and in a mechanical fashion; (11) the stimulus comprises the step of incubating the precursor cells with a receptor ligand cocktail; (12) the precursor cells are isolated from an ungulate animal and preferably a bovine animal; (13) the precursor cells are selected from the group consisting of non-embryonic cells, primordial germ cells, genital ridge cells, amniotic cells, fetal fibroblast cells, ovarian follicular cells, cumulus cells, hepatic cells, differentiated cells, cells that originate from an animal, embryonic stem cells, fetal cells, and embryonic cells; (14) the receptor ligand cocktail comprises at least one component selected from the group consisting of cytokine, growth factor, trophic factor, and neurotrophic factor, LIF, and FGF; (15) the LIF has an amino acid sequence substantially similar to the amino acid sequence of human LIF; and (16) the FGF has an amino acid sequence substantially similar to the amino acid sequence of bovine bFGF.

The terms "mechanical fashion" and "mechanical stimulus" as used herein refers to introducing a stimulus to cells where the stimulus is not introduced by feeder cells. For example, purified LIF and bFGF (defined hereafter) can be introduced as a stimulus to precursor cells by adding these purified products to a cell culture medium in which the precursor cells are growing.

The term "feeder cells" as used herein refers to cells grown in co-culture with target cells. Target cells can be precursor cells and totipotent cells, for example. Feeder cells can provide, for example, peptides, polypeptides, electrical signals, organic molecules (e.g., steroids), nucleic acid molecules, growth factors (e.g., bFGF), other factors (e.g., cytokines such as LIF and steel factor), and metabolic nutrients to target cells. Certain cells, such as immortalized, totipotent cells may not require feeder cells for healthy growth. Feeder cells preferably grow in a mono-layer.

Feeder cells can be established from multiple cell types. Examples of these cell types are fetal cells, mouse cells, Buffalo rat liver cells, and oviductal cells. These examples are not meant to be limiting. Tissue samples can be broken down to establish a feeder cell line by methods well known in the art (e.g., by using a blender). Feeder cells may originate from the same or different animal species as the precursor cells. In an example of feeder cells established from fetal cells, ungulate fetuses and preferably bovine fetuses may be utilized to establish a feeder cell line where one or more cell types have been removed from the fetus (e.g., primordial germs cells, cells in the head region, and cells in the body cavity region). When an entire fetus is utilized to establish a fetal feeder cell line, feeder cells (e.g., fibroblast cells) and precursor cells (e.g., primordial germ cells) can arise from the same source (e.g., one fetus).

The term "receptor ligand cocktail" as used herein refers to a mixture of one or more receptor ligands. A receptor ligand refers to any molecule that binds to a receptor protein located on the outside or the inside of a cell. Receptor ligands can be selected from molecules of the cytokine family of ligands, neurotrophin family of ligands, growth factor family of ligands, and mitogen family of ligands, all of which are well known to a person of ordinary skill in the art. Examples of receptor/ligand pairs are: epidermal growth factor receptor/epidermal growth factor, insulin/insulin receptor, cAMP-dependent protein kinase/cAMP, growth hormone receptor/growth hormone, and steroid receptor/steroid. It has been shown that certain receptors exhibit cross-reactivity. For example, heterologous receptors, such as insulin-like growth factor receptor 1 (IGFR1) and insulin-like growth factor receptor 2 (IGFR2) can both bind IGF1. When a receptor ligand cocktail comprises the stimulus, the receptor ligand cocktail can be introduced to the precursor cell in a variety of manners known to a person of ordinary skill in the art.

The term "cytokine" as used herein refers to a large family of receptor ligands well-known to a person of ordinary skill in the art. The cytokine family of receptor ligands includes such members as leukemia inhibitor factor (LIF), cardiotrophin 1 (CT-1), ciliary neurotrophic factor (CNTF), stem cell factor (SCF), oncostatin M (OSM), and any member of the interleukin (IL) family, including IL-6, IL-11, and IL-12. The teachings of the invention do not require the mechanical addition of steel factor (also known as stem cell factor in the art) for the conversion of precursor cells into totipotent cells.

The term "growth factor" as used herein refers to any receptor ligand that causes a cell growth and/or cell proliferation effect. Examples of growth factors are well known in the art. Fibroblast growth factor (FGF) is one example of a growth factor. The term "bFGF" can refer to basic FGF.

The term "substantially similar" as used herein in reference to amino acid sequences refers to two amino acid sequences having preferably 50% or more amino acid identity, more preferably 70% or more amino acid identity or most preferably 90% or more amino acid identity. Amino acid identity is a property of amino acid sequence that measures their similarity or relationship. Identity is measured by dividing the number of identical residues in the two sequences by the total number of residues and multiplying the product by 100. Thus, two copies of exactly the same sequence have 100% identity, while sequences that are less highly conserved and have deletions, additions, or replacements have a lower degree of identity. Those of ordinary skill in the art will recognize that several computer programs are available for performing sequence comparisons and determining sequence identity.

In another aspect, the invention features a method for preparing a totipotent mammalian cell, where the cell is immortalized, comprising the following steps: (a) isolating one or more precursor cells; and (b) introducing the precursor cell to a stimulus that converts the precursor cell into the totipotent cell. Any of the embodiments defined previously herein in reference to totipotent mammalian cells relate to the method for preparing a totipotent mammalian cell.

Cloned Totipotent Embryos of the Invention

The invention relates in part to cloned totipotent embryos. Hence, aspects of the invention feature cloned mammalian embryos where (1) the embryo is totipotent; (2) the embryo arises from an immortalized and/or totipotent cell; and (3) the embryo arises from a non-embryonic cell; and (4) any combination of the foregoing.

The term "totipotent" as used herein in reference to embryos refers to embryos that can develop into a live born animal. The term "live born" is defined previously.

The term "cloned" as used herein refers to a cell, embryonic cell, fetal cell, and/or animal cell having a nuclear DNA sequence that is substantially similar or identical to the nuclear DNA sequence of another cell, embryonic cell, fetal cell, and/or animal cell. The terms "substantially similar" and "identical" are described herein. The cloned embryo can arise from one nuclear transfer, or alternatively, the cloned embryo can arise from a cloning process that includes at least one re-cloning step. If the cloned embryo arises from a cloning procedure that includes at least one re-cloning step, then the cloned embryo can indirectly arise from an immortalized, totipotent cell since the re-cloning step can utilize embryonic cells isolated from an embryo that arose from an immortalized, totipotent cell.

In preferred embodiments, (1) the cloned mammalian embryo is preferably an ungulate embryo and more preferably a bovine embryo; (2) the cloned bovine embryo can be one member of a plurality of embryos, where the plurality of embryos share a substantially similar nuclear DNA sequence; (3) the cloned mammalian embryo can be one member of a plurality of embryos, and the plurality of embryos can have an identical nuclear DNA sequence; (4) the cloned mammalian embryo has a nuclear DNA sequence that is substantially similar to a nuclear DNA sequence of a live born mammalian animal; (5) one or more cells of the cloned mammalian embryo have modified nuclear DNA; (6) the cloned mammalian embryo is subject to manipulation; (7) the manipulation comprises the step of culturing the embryo in a suitable medium; (8) the suitable medium for culturing the embryo is CR-2 medium; (9) the medium can comprise feeder cells; (10) the manipulation of an embryo comprises the step of implanting the embryo into the uterus of a female; (11) the female animal is preferably an ungulate animal and more preferably a bovine animal; (12) the estrus cycle of the female is synchronized with the development cycle of the embryo; and (13) the manipulation comprises the step of incubating the embryo in an artificial environment.

All preferred embodiments related to modified nuclear DNA for totipotent cells of the invention extend to cloned embryos of the invention. In addition, any of the manipulations described in conjunction with totipotent cells of the invention apply to cloned embryos of the invention.

The term "substantially similar" as used herein in reference to nuclear DNA sequences refers to two nuclear DNA sequences that are nearly identical. The two sequences may differ by copy error differences that normally occur during the replication of a nuclear DNA. Substantially similar DNA sequences are preferably greater than 97% identical, more preferably greater than 98% identical, and most preferably greater than 99% identical. The term "identity" as used herein in reference to nuclear DNA sequences can refer to the same usage of the term in reference to amino acid sequences, which is described previously herein.

The term "plurality" as used herein in reference to embryos refers to a set comprising at least two embryos having a substantially similar nuclear DNA sequence. In preferred embodiments, the plurality consists of five or more embryos, ten or more embryos, one-hundred or more embryos, or one-thousand or more embryos. Because the occurrence of more than three embryos progressing to term only occurs with a probability of approximately 1/100,000, a plurality of at least five embryos or animals relates to cloned embryos or cloned animals rather than naturally occurring embryos or animals.

The term "culturing" as used herein with respect to embryos refers to laboratory procedures that involve placing an embryo in a culture medium. The embryo can be placed in the culture medium for an appropriate amount of time to allow the embryo to remain static but functional in the medium, or to allow the embryo to grow in the medium. Culture media suitable for culturing embryos are well-known to those skilled in the art. See, e.g., U.S. Pat. No. 5,213,979, entitled "In vitro Culture of Bovine Embryos," First et al., issued May 25, 1993, and U.S. Pat. No. 5,096,822, entitled "Bovine Embryo Medium," Rosenkrans, Jr. et al., issued Mar. 17, 1992, incorporated herein by reference in their entireties including all figures, tables, and drawings.

The term "suitable medium" as used herein refers to any medium that allows cell proliferation. The suitable medium need not promote maximum proliferation, only measurable cell proliferation. A suitable medium for embryo development is discussed previously.

The term "CR-2 medium" as used herein refers to a medium suitable for culturing embryos. CR-2 medium can comprise one or more of the following components: sodium chloride; potassium chloride; sodium bicarbonate; hemicalcium L-lactate; and fatty-acid free BSA. These components may exist in the medium in concentrations of about 115 mM for sodium chloride; about 3 mM for potassium chloride; about 25 mM for sodium bicarbonate; about 5 mM for hemicalcium L-lactate; and about 3 mg/mL for fatty-acid free BSA. Alternatively, the concentrations of these components may exist in the medium in concentrations of 0–1 M sodium chloride; 0–100 mM potassium chloride; 0–500 mM sodium bicarbonate; 0–100 mM hemicalcium L-lactate; and 0–100 mg/mL fatty-acid free BSA.

The term "feeder cells" is defined previously herein. Embryos of the invention can be cultured in media with or without feeder cells. In other preferred embodiments, the feeder cells can be cumulus cells.

The term "implanting" as used herein in reference to embryos refers to impregnating a female animal with an embryo described herein. This technique is well known to a person of ordinary skill in the art. See, e.g., Seidel and Elsden, 1997, *Embryo Transfer in Dairy Cattle*, W. D. Hoard & Sons, Co., Hoards Dairyman. The embryo may be allowed to develop in utero, or alternatively, the fetus may be removed from the uterine environment before parturition.

The term "synchronized" as used herein in reference to estrus cycle, refers to assisted reproductive techniques well known to a person of ordinary skill in the art. These techniques are fully described in the reference cited in the previous paragraph. Typically, estrogen and progesterone hormones are utilized to synchronize the estrus cycle of the female animal with the developmental cycle of the embryo. The term "developmental cycle" as used herein refers to embryos of the invention and the time period that exists between each cell division within the embryo. This time period is predictable for embryos from ungulates, and can be synchronized with the estrus cycle of a recipient animal.

The term "artificial environment" refers to one that promotes the development of an embryo or other developing cell mass. An artificial environment can be a uterine environment or an oviductal environment of a species different from that of the developing cell mass. For example, a developing bovine embryo can be placed into the uterus or oviduct of an ovine animal. Stice & Keefer, 1993, "Multiple generational bovine embryo cloning," *Biology of Reproduction* 48: 715–719. Alternatively, an artificial development environment can be assembled in vitro. This type of artificial uterine environment can be synthesized using biological and chemical components known in the art.

In another aspect the invention features a cloned mammalian embryo, where the embryo is totipotent, prepared by a process comprising the step of nuclear transfer. Preferably, nuclear transfer occurs between (a) a totipotent mammalian cell, where the cell is immortalized, and (b) an oocyte, where the oocyte is at a stage allowing formation of the embryo.

In preferred embodiments, (1) the oocyte is an enucleated oocyte; (2) the totipotent mammalian cell and the oocyte preferably originate from an ungulate animal and more preferably originate from a bovine animal; (3) the totipotent mammalian cell can originate from one specie of ungulate and the oocyte can originate from another specie of ungulate; (4) the oocyte is a young oocyte; (5) the totipotent mammalian cell is placed in the perivitelline space of the oocyte; (6) the totipotent cell utilized for nuclear transfer can arise from any of the cells described previously (e.g., a non-embryonic cell, a primordial germ cell, a genital ridge cell, a differentiated cell, a fetal cell, a non-fetal cell, a non-primordial germ cell, an amniotic cell, a fetal fibroblast cell, an ovarian follicular cell, a cumulus cell, an hepatic cell, a cell isolated from an asynchronous population of cells, a cell isolated from a synchronous population of cells, a cell isolated from an existing animal, and an embryonic stem cell); (7) the nuclear transfer comprises the step of translocation of the totipotent mammalian cell into the recipient oocyte; (8) the translocation can comprise the step of injection of the totipotent mammalian cell nuclear donor into the recipient oocyte; (9) the translocation can comprise the step of fusion of the totipotent mammalian cell and the oocyte; (10) the fusion can comprise the step of delivering one or more electrical pulses to the totipotent mammalian cell and the oocyte; (11) the fusion can comprise the step of delivering a suitable concentration of at least one fusion agent to the totipotent mammalian cell and the oocyte; (12) the nuclear transfer may comprise the step of activation of the totipotent mammalian cell and the oocyte; and (13) the activation is accomplished by introducing DMAP and/or Ionomycin to an oocyte and/or a cybrid.

The term "enucleated oocyte" as used herein refers to an oocyte which has had part of its contents removed. Typically a needle can be placed into an oocyte and the nucleus can be aspirated into the inner space of the needle. The needle can be removed from the oocyte without rupturing the plasma membrane. This enucleation technique is well known to a person of ordinary skill in the art. See, U.S. Pat. No. 4,994,384; U.S. Pat. No. 5,057,420; and Willadsen, 1986, *Nature* 320:63–65. An enucleated oocyte can be prepared from a young or an aged oocyte. Definitions of "young oocyte" and "aged oocyte" are provided herein. Nuclear transfer may be accomplished by combining one nuclear donor and more than one enucleated oocyte. In addition, nuclear transfer may be accomplished by combining one nuclear donor, one or more enucleated oocytes, and the cytoplasm of one or more enucleated oocytes.

The term "cybrid" as used herein refers to a construction where an entire nuclear donor is translocated into the cytoplasm of a recipient oocyte. See, e.g., *In Vitro Cell. Dev. Biol.* 26: 97–101 (1990).

The invention specifically relates to cloned mammalian embryos created by nuclear transfer, where the nucleus of the oocyte is not physically extracted from the nucleus. It is possible to create a cloned embryo where the nuclear DNA from the donor cell is the material replicated during cellular divisions. See, e.g., Wagoner et al., 1996, "Functional enucleation of bovine oocytes: effects of centrifugation and ultraviolet light," *Theriogenology* 46: 279–284.

The term "another ungulate" as used herein refers to a situation where the nuclear donor originates from an ungulate of a different species, genera or family than the ungulate from which the recipient oocyte originates. For example, the totipotent mammalian cell used as a nuclear donor can arise from a water buffalo, while the oocyte recipient can arise from a domestic cow. This example is not meant to be limiting and any ungulate species/family combination of nuclear donors and recipient oocytes are foreseen by the invention.

The term "young oocyte" as used herein refers to an oocyte that has been matured in vitro and/or ovulated in vivo for less than 28 hours since the onset of maturation. Oocytes can be isolated from live animals using methods well known to a person of ordinary skill in the art. See, e.g., Picterse et al., 1988, "Aspiration of bovine oocytes during transvaginal ultrasound scanning of the ovaries," *Theriogenology* 30: 751–762. Oocytes can be isolated from ovaries or oviducts or deceased or live born animals. Suitable media for in vitro culture of oocytes are well known to a person of ordinary skill in the art. See, e.g., U.S. Pat. No. 5,057,420, which is incorporated by reference herein.

The term "maturation" as used herein refers to process in which an oocyte is incubated in a medium in vitro. Oocytes can be incubated with multiple media well known to a person of ordinary skill in the art. See, e.g., Saito et al., 1992, *Roux's Arch. Dev. Biol.* 201: 134–141 for bovine organisms and Wells et al., 1997, *Biol. Repr.* 57: 385–393 for ovine organisms, both of which are incorporated herein by reference in their entireties including all figures, tables, and drawings. Maturation media can comprise multiple types of components, including microtubule inhibitors (e.g., cytochalasin B). Other examples of components that can be incorporated into maturation media are discussed in WO 97/07668, entitled "Unactivated Oocytes as Cytoplast Recipients for Nuclear Transfer," Campbell & Wilmut, published on Mar. 6, 1997, hereby incorporated herein by reference in its entirety, including all figures, tables, and drawings. The time of maturation can be determined from the time that an oocyte is placed in a maturation medium and the time that the oocyte is then utilized in a nuclear transfer procedure.

Young oocytes can be identified by the appearance of their ooplasm. Because certain cellular material (e.g., lipids) have not yet dispersed within the ooplasm. Young oocytes can have a pycnotic appearance. A pycnotic appearance can be characterized as clumping of cytoplasmic material. A "pycnotic" appearance is to be contrasted with the appearance of oocytes that are older than 28 hours, which have a more homogenous appearing ooplasm.

The term "translocation" as used herein in reference to nuclear transfer refers to the combining of a totipotent mammalian cell nuclear donor and a recipient oocyte. The translocation may be performed by such techniques as fusion and/or direct injection, for example.

The term "injection" as used herein in reference to embryos, refers to the perforation of the oocyte with a needle, and insertion of the nuclear donor in the needle into the oocyte. In preferred embodiments, the nuclear donor may be injected into the cytoplasm of the oocyte or in the perivitelline space of the oocyte. This direct injection approach is well known to a person of ordinary skill in the art, as indicated by the publications already incorporated herein in reference to nuclear transfer. For the direct injection approach to nuclear transfer, the whole totipotent mammalian cell may be injected into the oocyte, or alternatively, a nucleus isolated from the totipotent mammalian cell may be injected into the oocyte. Such an isolated nucleus may be surrounded by nuclear membrane only, or the isolated nucleus may be surrounded by nuclear membrane and plasma membrane in any proportion. The oocyte may be pre-treated to enhance the strength of its plasma membrane, such as by incubating the oocyte in sucrose prior to injection of the nuclear donor.

Techniques for placing a nuclear donor (e.g., an immortalized and totipotent cell of the invention) into the perivitelline space of an enucleated oocyte are well known to a person of ordinary skill in the art, and are fully described in the patents and references cited previously herein in reference to nuclear transfer.

The term "fusion" as used herein refers to the combination of portions of lipid membranes corresponding to the totipotent mammalian cell nuclear donor and the recipient oocyte. Lipid membranes can correspond to the plasma membranes of cells or nuclear membranes, for example. The fusion can occur between the nuclear donor and recipient oocyte when they are placed adjacent to one another, or when the nuclear donor is placed in the perivitelline space of the recipient oocyte, for example. Specific examples for translocation of the totipotent mammalian cell into the oocyte are described hereafter in other preferred embodiments. These techniques for translocation are fully described in the references cited previously herein in reference to nuclear transfer.

The term "electrical pulses" as used herein refers to subjecting the nuclear donor and recipient oocyte to electric current. For nuclear transfer, the nuclear donor and recipient oocyte can be aligned between electrodes and subjected to electrical current. The electrical current can be alternating current or direct current. The electrical current can be delivered to cells for a variety of different times as one pulse or as multiple pulses. The cells are typically cultured in a suitable medium for the delivery of electrical pulses. Examples of electrical pulse conditions utilized for nuclear transfer are described in the references and patents previously cited herein in reference to nuclear transfer.

The term "fusion agent" as used herein refers to any compound or biological organism that can increase the probability that portions of plasma membranes from different cells will fuse when a totipotent mammalian cell nuclear donor is placed adjacent to the recipient oocyte. In preferred embodiments fusion agents are selected from the group consisting of polyethylene glycol (PEG), trypsin, dimethylsulfoxide (DMSO), lectins, agglutinin, viruses, and Sendai virus. These examples are not meant to be limiting and other fusion agents known in the art are applicable and included herein.

The term "suitable concentration" as used herein in reference to fusion agents, refers to any concentration of a fusion agent that affords a measurable amount of fusion. Fusion can be measured by multiple techniques well known to a person of ordinary skill in the art, such as by utilizing a light microscope, dyes, and fluorescent lipids, for example.

The term "activation" refers to any materials and methods useful for stimulating a cell to divide before, during, and after a nuclear transfer step. Cybrids may require stimulation in order to divide after a nuclear transfer has occurred. The invention pertains to any activation materials and methods known to a person of ordinary skill in the art. Although electrical pulses are sometimes sufficient for stimulating activation of cybrids, other means are sometimes useful or necessary for proper activation of the cybrid. Chemical materials and methods useful for activating embryos are described below in other preferred embodiments of the invention.

Examples of non-electrical means for activation include agents such as ethanol; inositol trisphosphate ($IP_3$); $Ca^{++}$ ionophores (e.g., ionomycin) and protein kinase inhibitors (e.g., 6-dimethylaminopurine (DMAP)) ; temperature change; protein synthesis inhibitors (e.g., cyclohexamide); phorbol esters such as phorbol 12-myristate 13-acetate (PMA); mechanical techniques; and thapsigargin. The invention includes any activation techniques known in the art. See, e.g., U.S. Pat. No. 5,496,720, entitled "Parthenogenic Oocyte Activation," issued on Mar. 5, 1996, Susko-Parrish et al., incorporated by reference herein in its entirety, including all figures, tables, and drawings.

In other preferred embodiments, (1) one or more cells of the cloned embryo comprise modified nuclear DNA; (2) the cloned embryo is subject to manipulation; (3) the manipulation comprises the step of disaggregating at least one individual cell from a cloned embryo; (4) the manipulation comprises the step of utilizing the individual cell as a nuclear donor in a nuclear transfer procedure; (5) the individual cell is disaggregated from the inner cell mass of a blastocyst stage embryo; (6) the individual cell is disaggregated from a pre-blastocyst stage embryo; (7) the manipulation comprises the process of re-cloning; (8) the re-cloning process comprises the steps of: (a) separating the embryo into one or more individual cells, and (b) performing at least one subsequent nuclear transfer between (i) an individual cell of (a), and (ii) an oocyte; (9) the oocyte utilized for the subsequent nuclear transfer is an aged oocyte; (10) the individual cell is placed in the perivitelline space of the enucleated oocyte for the subsequent nuclear transfer; (11) the subsequent nuclear transfer comprises at least one of the steps of translocation, injection, fusion, and activation of the individual cell and/or the enucleated oocyte; (12) one or more cells of the cloned mammalian embryo arising from the subsequent nuclear transfer comprises modified nuclear DNA; and (13) the cloned mammalian embryo arising from the subsequent nuclear transfer may be subject to a subsequent manipulation, where the subsequent manipulation is any of the manipulation steps defined previously herein in relation to immortalized cells and/or cloned embryos.

The term "individual cells" as used herein refers to cells that have been isolated from a cloned mammalian embryo of the invention. An individual single cell can be isolated from the rest of the embryonic mass by techniques well known to those skilled in the art. See, U.S. Pat. Nos. 4,994,384 and 5,957,420, previously incorporated herein by reference in their entireties.

The term "subsequent nuclear transfer" as described herein is also referred to as a "re-cloning" step. Preferably, a re-cloning step can be utilized to enhance nuclear reprogramming during nuclear transfer, such that the product of nuclear transfer is a live born animal. The re-cloning step is distinct, since previous efforts towards re-cloning have been directed to multiplying embryo number and not for enhancement of nuclear reprogramming. The number of subsequent nuclear transfer steps is discussed in greater detail hereafter.

Any of the preferred embodiments related to the translocation, injection, fusion, and activation steps described previously herein relate to the subsequent nuclear transfer step.

The term "inner cell mass" as used herein refers to the cells that gives rise to the embryo proper. The cells that line the outside of a blastocyst are referred to as the trophoblast of the embryo. The methods for isolating inner cell mass cells from an embryo are well known to a person of ordinary skill in the art. See, Sims and First, 1993, *Theriogenology* 39:313; and Keefer et al., 1994, *Mol. Reprod. Dev.* 38:264–268, hereby incorporated by reference herein in their entireties, including all figures, tables, and drawings. The term "pre-blastocyst" is well known in the art and is referred to previously.

The term "aged oocyte" as used herein refers to an oocyte that has been matured in vitro or ovulated in vivo for more than 28 hours since the onset of maturation or ovulation. An aged oocyte can be identified by its characteristically homogenous ooplasm. This appearance is to be contrasted with the pycnotic appearance of young oocytes as described previously herein. The age of the oocyte can be defined by the time that has elapsed between the time that the oocyte is placed in a suitable maturation medium and the time that the oocyte is activated. The age of the oocyte can dramatically enhance the efficiency of nuclear transfer.

The term "ovulated in vivo" as used herein refers to an oocyte that is isolated from an animal a certain number of hours after the animal exhibits characteristics that it is in estrus. The characteristics of an animal in estrus are well known to a person of ordinary skill in the art, as described in references disclosed herein.

In another aspect the invention relates to a method for preparing a cloned mammalian embryo. The method comprises the step of a nuclear transfer between: (a) a totipotent mammalian cell, where the cell is immortalized; and (b) an oocyte, where the oocyte is at a stage allowing formation of the embryo. In preferred embodiments, any of the embodiments of the invention concerning cloned mammalian embryos apply to methods for preparing cloned mammalian embryos.

Cloned Fetuses of the Invention

In another aspect, the invention features cloned mammalian fetuses arising from totipotent embryos of the invention. Preferably, the mammalian fetuses are ungulate fetuses, and more preferably, the ungulate fetuses are bovine fetuses. A fetus may be isolated from the uterus of a pregnant female animal.

In preferred embodiments, (1) one or more cells of the fetuses harbor modified nuclear DNA (defined previously herein); and (2) the fetuses may be subject to any of the manipulations defined herein. For example, one manipulation may comprise the steps of isolating a fetus from the uterus of a pregnant female animal, isolating a cell from the fetus (e.g., a primordial germ cell), and utilizing the isolated cell as a nuclear donor for nuclear transfer.

Other aspects of the invention feature (1) a cloned mammalian fetus prepared by a process comprising the steps of (a) preparation of a cloned mammalian embryo defined previously, and (b) manipulation of the cloned mammalian embryo such that it develops into a fetus; (2) a method for preparing a cloned mammalian fetus comprising the steps of (a) preparation of a cloned mammalian embryo defined previously, and (b) manipulation of the cloned mammalian embryo such that it develops into a fetus; (3) a method of using a cloned fetus of the invention comprising the step of isolating at least one cell type from a fetus (e.g., for creating a feeder cell layer); and (4) a method of using a cloned fetus of the invention comprising the step of separating at least one part of a fetus into individual cells (e.g., for establishing a feeder cell layer).

Cloned Animals of the Invention

In another aspect the invention features a cloned mammalian animal arising from a cloned embryo of the invention. The embryo is totipotent and can arise from any of the processes or methods described previously herein.

In preferred embodiments, the cloned mammalian animal (1) is preferably a cloned ungulate animal and more preferably a cloned bovine animal; and (2) is equal in age or older than an animal selected from the group consisting of pre- and post-pubertal animals.

In yet another aspect the invention relates to a cloned mammalian animal, where the animal is one member of a plurality of animals, and where the plurality of animals have a substantially similar nuclear DNA sequence. The term "substantially similar" in relation to nuclear DNA sequences is defined previously herein.

In preferred embodiments, (1) the plurality consists of five or more animals, ten or more animals, one-hundred or more animals, and one-thousand or more animals; and (2) the plurality of animals can have an identical nuclear DNA sequence. The term "identical" in reference to nuclear DNA sequences is described previously herein.

In another aspect, the invention relates to a cloned mammalian animal having one or more cells that comprise modified nuclear DNA. All of the preferred embodiments relating to modified nuclear DNA described previously apply to cloned bovine animals of the invention.

In yet another aspect, the invention features a method of using a cloned mammalian animal, comprising the step of isolating at least one component from the mammalian animal.

The term "component" as used herein refers to any portion of an animal. A component can be selected from the group consisting of fluid, biological fluid, cell, tissue, organ, gamete, embryo, and fetus. Precursor cells may arise from fluids, biological fluids, cells, tissues, organs, gametes, embryos, and fetuses isolated from cloned organisms of the invention.

The term "gamete" as used herein refers to any cell participating, directly or indirectly, to the reproductive system of an animal. Examples of gametes are spermatocytes, spermatogonia, oocytes, and oogonia. Gametes can be present in fluids, tissues, and organs collected from animals (e.g., sperm is present in semen). For example, methods of collecting semen for the purposes of artificial insemination are well known to a person of ordinary skill in the art. See, e.g., *Physiology of Reproduction and Artificial Insemination of Cattle* (2nd edition), Salisbury et al., copyright 1961, 1978, W H Freeman & Co., San Francisco. However, the invention relates to the collection of any type of gamete from an animal.

The term "tissue" is defined previously. The term "organ" refers to any organ isolated from an animal or any portion of an organ. Examples of organs and tissues are neuronal tissue, brain tissue, spleen, heart, lung, gallbladder, pancreas, testis, ovary and kidney. These examples are not limiting and the invention relates to any organ and any tissue isolated from a cloned animal of the invention.

In a preferred embodiments, the invention relates to (1) fluids, biological fluids, cells, tissues, organs, gametes, embryos, and fetuses can be subject to manipulation; (2) the manipulation can comprise the step of cryopreserving the gametes, embryos, and/or fetal tissues; (3) the manipulation can comprise the step of thawing the cryopreserved items; (4) the manipulation can comprise the step of separating the semen into X-chromosome bearing semen and Y-chromosome bearing semen; (5) the manipulation comprises methods of preparing the semen for artificial insemination; (6) the manipulation comprises the step of purification of a desired polypeptide(s) from the biological fluid or tissue; (7) the manipulation comprises concentration of the biological fluids or tissues; and (8) the manipulation can comprise the step of transferring one or more cloned cells, cloned tissues, cloned organs, and/or portions of cloned organs to a recipient organism (e.g., the recipient organism may be of a different specie than the donor source).

The term "separating" as used herein in reference to separating semen refers to methods well known to a person skilled in the art for fractionating a semen sample into sex-specific fractions. This type of separation can be accomplished by using flow cytometers that are commercially available. Methods of utilizing flow cytometers from separating sperm by genetic content are well known in the art. In addition, semen can be separated by its sex-associated characteristics by other methods well known to a person of ordinary skill in the art. See, U.S. Pat. Nos. 5,439,362, 5,346,990, and 5,021,244, entitled "Sex-Associated Membrane Proteins and Methods for Increasing the Probability that Offspring Will Be of a Desired Sex," Spaulding, issued on Aug. 8, 1995, Sep. 13, 1994, and Jun. 4, 1991 respectively, all of which are incorporated herein by reference in their entireties including all figures, tables, and drawings.

Semen preparation methods are well known to someone of ordinary skill in the art. Examples of these preparative steps are described in *Physiology of Reproduction and Artificial Insemination of Cattle* (2nd. edition), Salisbury et al., copyright 1961, 1978, W. H. Freeman & Co., San Francisco.

The term "purification" as used herein refers to increasing the specific activity of a particular polypeptide or polypeptides in a sample. In preferred embodiments, specific activity is expressed as the ratio between the activity of the target polypeptide and the concentration of total polypeptide in the sample. Activity can be catalytic activity and/or binding activity, for example. In other preferred embodiments, specific activity is expressed as the ratio between the concentration of the target polypeptide and the concentration of total polypeptide. Purification methods include dialysis, centrifugation, and column chromatography techniques, which are well-known procedures to a person of ordinary skill in the art. See, e.g., Young et al., 1997, "Production of biopharmaceutical proteins in the milk of transgenic dairy animals," *BioPharm* 10(6): 34–38.

The term "transferring" as used herein refers to shifting a group of cells, tissues, organs, and/or portions of organs to an animal. The cells, tissues, organs, and/or portions of organs can be, for example, (a) developed in vitro and then transferred to an animal, (b) removed from an animal and transferred to another animal of a different specie, (c) removed from an animal and transferred to another animal of the same specie, (d) removed from one portion of an animal (e.g., the leg of an animal) and then transferred to another portion of the same animal (e.g., the brain of the animal), and/or (e) any combination of the foregoing. The term "transferring" refers to adding cells, tissues, and/or organs to an animal and can also relate to removing cells, tissues, and/or organs from an animal and replacing them with cells, tissues, and/or organs from another source.

The term "transferring" as used herein also refers to implanting one or more cells, tissues, organs, and/or portions of organs from the cloned mammalian animal into another organism. For example, neuronal tissue from a cloned mammalian organism can be grafted into an appropriate area in the human nervous system to treat neurological diseases such as Alzheimer's disease. Alternatively, cloned cells, tissues, and/or organs originating from a porcine organism may be transferred to a human recipient. Surgical methods for accomplishing this preferred aspect of the invention are well known to a person of ordinary skill in the art. Transferring procedures may include the step of removing cells, tissues, or organs from a recipient organism before a transfer step.

In other aspects the invention features (1) a cloned mammalian animal prepared by a process comprising the steps of: (a) preparation of a cloned mammalian embryo by any one of the methods described herein for producing such a cloned mammalian embryo, and (b) manipulation of the cloned mammalian embryo such that it develops into a live born animal; (2) a process comprising the steps of: (a) preparation of a cloned mammalian embryo by any one of the methods described herein for preparing such a cloned mammalian embryo, and (b) manipulation of the cloned mammalian embryo such that it develops into a live born animal; and (3) a cloned mammalian animal, comprising the steps of: (a) preparation of a cloned mammalian embryo by any one of the methods for producing such an embryo described herein, and (b) manipulation of the cloned mammalian embryo such that it develops into a live born animal.

In preferred embodiments, (1) the live born animal is preferably an ungulate animal and more preferably a bovine animal; (2) the manipulation can comprise the step of implanting the embryo into a uterus of an animal; (3) the estrus cycle of the animal can be synchronized to the developmental stage of the embryo; and (4) the manipulation can comprise the step of implanting the embryo into an artificial environment.

The summary of the invention described above is not limiting and other features and advantages of the invention will be apparent from the following detailed description of the preferred embodiments, as well as from the claims.

DETAILED DESCRIPTION OF THE PREFERRED EMBODIMENTS

Figure 1:
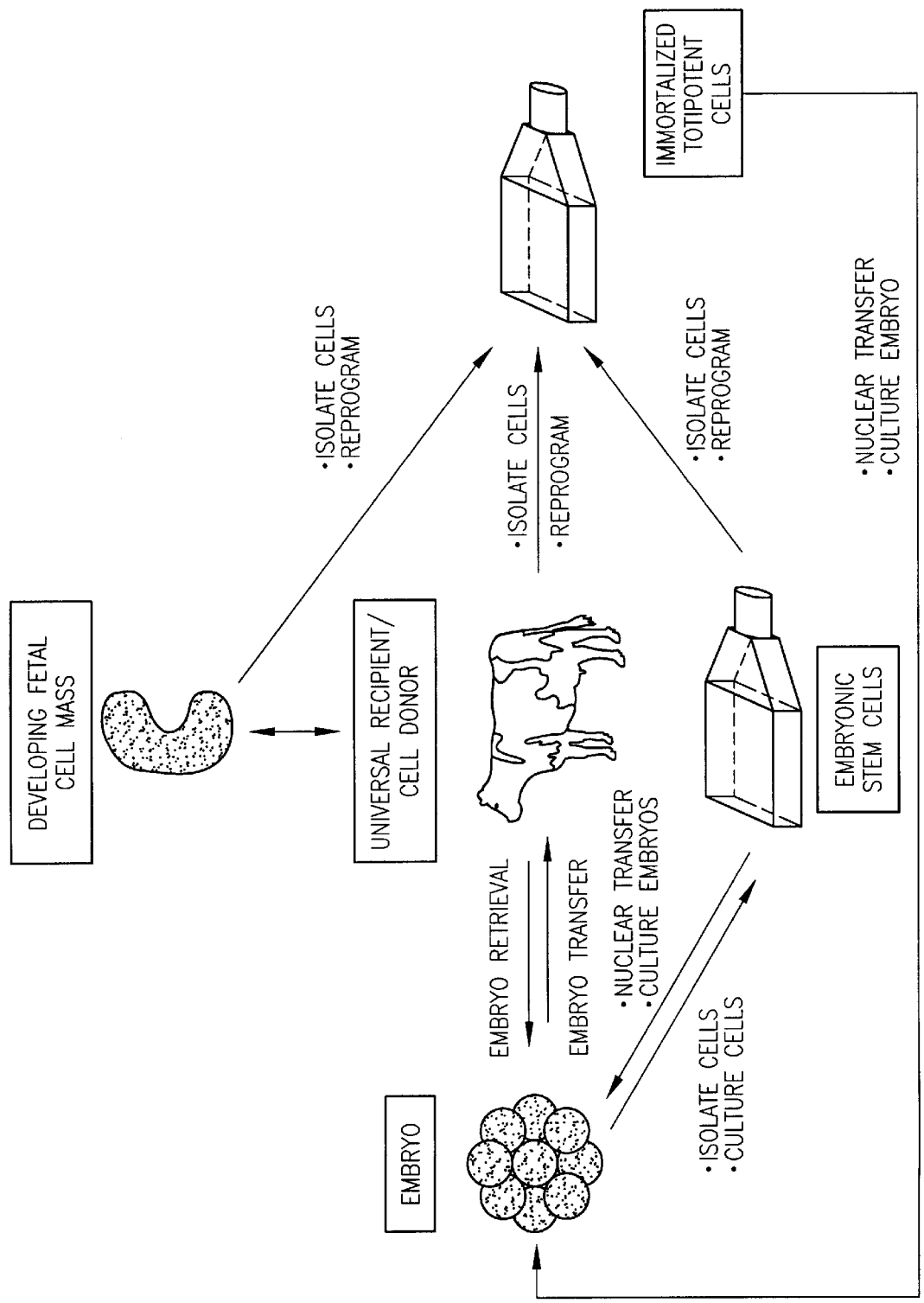
FIG. 1 illustrates multiple embodiments of the invention relating to the generation of immortalized, totipotent cells from precursor cells. The figure indicates that immortalized, totipotent cells can arise from embryonic stem cells, primordial germ cells, and cells isolated from an animal. The precursor cell sources illustrated by FIG. I are not limiting and other precursor cell sources are described herein.

The present invention relates to cloning technologies. The present invention provides multiple advantages over the tools and methods currently utilized in the field of cloning technology. For example, the invention relates in part to immortalized, totipotent cells useful for cloning animals. These immortalized, totipotent cells can give rise to methods of producing cloned animals by utilizing virtually any type of cell. For example, cells isolated from a live born animal can be reprogrammed into immortalized, totipotent cells. This feature of the invention provides the ability to assess the phenotype of an existing animal and then readily establish a permanent cell line for cloning that animal. As described previously herein, no methods in the art have allowed for such advantages.

In addition, the immortalized, totipotent cells of the invention allow for creating permanent cell lines from virtually any type of cell. This reprogramming method is described previously herein. These permanent cell lines offer a nearly unlimited source of donor cells for nuclear transfer cloning techniques. Moreover, this feature provides the advantage of enhancing cloning efficiency due to the lower differentiation rates of these cell lines than existing cell lines used for cloning. For example, embryonic stem cell lines can harbor multiple colonies of cells that are not totipotent. The totipotent, immortalized cells of the invention harbor a higher percentage of totipotent cells than cell lines previously reported.

Moreover, the methods and processes for creating the immortalized, totipotent cells, totipotent cloned embryos, and cloned animals of the invention demonstrate the enhanced cloning efficiency over cloning tools and techniques previously reported. In particular, the totipotent, immortalized cell lines and the refined nuclear transfer techniques of the invention provide for this enhanced cloning efficiency. This enhanced efficiency satisfies a long felt need in the art.

I. Immortalized and Totipotent Cells

A. Generation of Immortalized and Totipotent Cells

Immortalized, totipotent cells of the invention can be produced from virtually any type of precursor cell. Preferred embodiments of the invention relate to the following types of precursor cells: (1) embryos arising from the union of two gametes in vitro or in vivo; (2) embryonic stem cells (ESC's) arising from embryos (e.g., pre-blastocyst cells and inner cell mass cells); (3) cultured and non-cultured cells derived from the inner cell mass of embryos; (4) cultured and non-cultured cells arising from a fetus; (5) primordial germ cells arising from a developing cell mass (e.g., genital ridge cells); (6) immortalized cultured cells arising from primordial germ cells, where the immortalized cells are referred to as embryonic germ cells (EGCs) in the art; (7) cultured and non-cultured cells obtained from amniotic fluid; (8) cultured and non-cultured cells arising from an ovarian follicle (e.g., cumulus cells); (9) cultured and non-cultured cells arising from a liver (e.g., hepatocytes); and (10) cultured and non-cultured cells isolated from an animal.

ESCs and EGCs can be readily generated from methods known in the art. See, e.g., Stice et al., 1996, *Biology of Reproduction* 54: 100–110, hereby incorporated by reference herein in its entirety including all figures, tables, and drawings. See also, Strelchenko, 1996, *Theriogenology* 45: 130–141. ESCs have been demonstrated to give rise to fetuses, from which primordial germ cells and EGCs can be derived. Therefore, ESCs are a nearly unlimited source for primordial germ cells and EGCs.

Cells derived from an animal can be isolated from nearly any type of tissue. For example, an ear-punch can be taken from an animal, the cells from the sample can be separated, and the separated cells can be subsequently cultured in vitro by using cell culture techniques well known to a person of ordinary skill in the art. Preferably, cells of the invention are extracted from bovine animals. Examples of materials and methods for reprogramming primary culture cells into immortalized, totipotent cells are described in exemplary embodiments hereafter.

Although exemplary embodiments of the invention are directed to bovine animals, materials and methods of the invention can be applied to the generation of immortalized, totipotent cells using precursor cells isolated from any mammal. Preferably immortalized, totipotent cells are extracted from ungulates. Examples of preferred ungulates envisioned for the invention are described previously.

Immortalized, totipotent cells of the invention are preferably generated from the examples of cells indicated in the preceding paragraph after treatment with a receptor ligand cocktail. Examples of receptor ligands are well known to a person of ordinary skill in the art. Cytokines and/or growth factors are preferred receptor ligands of the invention. See, e.g., R&D Systems Catalog, 614 McKinley Place N. E., Minneapolis, Minn. 55413. In exemplary embodiments, varying amounts of human recombinant leukemia inhibitory factor (hrLIF) and basic bovine fibroblast growth factor (bFGF) can be added to the culture medium to reprogram the precursor cells into immortalized, totipotent cells. Varying concentrations of these two cytokines can be added to the culture medium, preferably in concentrations of 1–1000 ng/mL, more preferably in concentrations between 10–500 ng/mL, and most preferably about 100 ng/mL. Exogenous soluble and membrane-associated forms of steel factor are not required for converting precursor cells into totipotent, immortalized cells.

These examples are not meant to be limiting and any cytokine or combination of cytokines can be added or deleted from those described in exemplary embodiments described hereafter. Preferred cytokines for generating immortalized, totipotent cells can be selected from the group consisting of fibroblast growth factor (FGF), leukemia inhibitor factor (LIF), cardiotrophin 1 (CT-1), ciliary neurotrophic factor (CNTF), stem cell factor (SCF), oncostatin M (OSM), and any member of the interleukin (IL) family, including IL-6, IL-11, and IL-12.

Other cytokines and other molecules besides cytokines can be added or deleted from the receptor ligand cocktail described in the exemplary embodiments described hereafter to create immortalized, totipotent cells from any of the cells described in the previous paragraph. Any of the conditions for generating immortalized, totipotent cells can be modified from those described herein. The ability of these modified conditions to generate immortalized, totipotent cells can be monitored by methods defined in the section "Identification of Immortalized and Totipotent Cells" described hereafter.

B. Culturing Immortalized and Totipotent Cells

A variety of methods for culturing cells exist in the art. See, e.g., *Culture of animal cells: a manual of basic technique* (2nd. edition), Freshney, copyright 1987, Alan R. Liss, Inc., New York. Particularly the cells that are precursor cells for immortalized, totipotent cells, as well as the immortalized, totipotent cells themselves, can be grown on feeder layers. Examples of feeder layers are well known to a person of ordinary skill in the art, and can arise from a number of different cells that are cultured in vitro. See, e.g., Strelchenko, 1996, *Theriogenology* 45: 130–141, as well as exemplary embodiments described hereafter. However, precursor cells for immortalized, totipotent cells as well as the immortalized, totipotent cells themselves need not be grown on feeder layers.

C. Identification of Immortalized and Totipotent Cells
    Identification of Immortalized Cells Immortalized cells can be identified as those that are not confined to the Hayflick limit. The Hayflick limit is defined by cells that divide for more than 60 cell divisions. Hence, cells that have divided for more than 60 cell divisions are immortalized cells. In addition, immortalized cells typically can be passaged at lower cell densities than non-immortalized cells.

The materials and methods described above (e.g., culturing the cells with cytokines) can convert non-immortalized cells into immortalized cells. Other methods exist in the art for generating immortalized cell lines from primary cells. For example, manipulating the activity of telomerase within the cells can immortalize cells. See, e.g., U.S. Pat. No. 5,645,986, entitled "Therapy and Diagnosis of Conditions Related to Telomere Length and/or Telomerase Activity," West et al., issued Jul. 8, 1997, and hereby incorporated by reference herein in its entirety including all figures, drawings, and tables.

Moreover, cellular immortality can be determined by identifying both low molecular weight and macromolecular markers that are specific for immortalized cells. The existence or lack of existence of a marker can be a determination of cell immortalization. In addition, a phenomenon associated with a marker can be an indication of immortality. For example, if the marker is an enzyme, an indication of the presence of the enzyme and/or a certain level of catalytic activity of that enzyme may be a suitable indication that a certain cell type is immortalized.

Low molecular weight markers include specific nucleosides, lipid associated sialic acids, polyamines, and pseudouridine. These examples are not limiting and the invention relates to any other low molecular weight markers known in the art.

Macromolecular markers can be separated into several classes including nucleic acid polymers, peptides, polypeptides, proteins, enzymes, growth factors, growth factor receptors, hormones, hormone receptors, oncogenes, oncogene products, and specific glycoproteins. Macromolecular markers can be selected from the group consisting of extracellular proteins, membrane associated proteins, and/or intracellular proteins, which may be membrane associated or soluble. One such marker for immortalized cells is telomerase or its associated activity, for example. See, U.S. Pat. No. 5,645,986, supra. Other examples of markers specific for immortalized cells can be selected from the following list:

1) Epidermal growth factor (EGF) and its receptor (EGF-R)
2) Transforming growth factor-alpha (TGF-alpha) and its receptor
3) c-erbB2 receptor tyrosine kinase (HER2 product)
4) Hyaluronan receptor (probably CD44, an integral membrane glycoprotein)
5) Carcinoembryonic antigen (CEA) family of tumor markers (for example T1, a glycosylated protein)
6) Telomerase, a ribonucleoprotein which maintains telomere length in immortalized cells
7) Phosphatases: placental alkaline phosphatase (PLAP), germ cell alkaline phosphatase, prostate acid phosphatase (PAS)
8) Cathepsin D (catalyzes degradation of laminin).
9) Ornithine decarboxylase (ODC) (catalyzes the rate-limiting step in polyamine synthesis)
10) Beta-glucuronidase
11) Alpha-6 integrin
12) Keratin K8
13) Oncogene products: ras oncogenes (k-ras, Ha-ras, p21), v-src, c-myc
14) Cyclin D1, cyclin A, and Retinoblastoma Gene Protein (Rb)
15) Changes in p53 expression or p53 mutations
16) Heterogeneous ribonucleoprotein-A2 (hnRNP-A2) overexpression
17) L-plastin
18) Ganglioside fucosyl-GM1
19) Mob-1 expression (mob-1) (homology to proinflammatory cytokines)

These examples are not limiting and the invention relates to any markers specific for immortalized cells that are known in the art.

In addition to markers for immortalization known in the art, markers for immortalization can be identified using methods well known in the art. For example, immortalization markers can be identified by analyzing particular molecules (e.g., nucleic acid molecules and polypeptide molecules) that are unique to specific cell types.

In examples pertaining to nucleic acid immortalization markers, immortalized and non-immortalized cells may be subjected to analysis for nucleic acid sequence content (e.g., hybridization techniques with nucleic acid probes). Nucleic acid samples from particular immortalized cells and nucleic acid samples from particular non-immortalized cells can be screened for particular nucleic acid sequences. If samples from non-immortalized cells lack a nucleic acid sequence present in immortalized cells, then this nucleic acid sequence could be a marker for distinguishing immortalized cells from non-immortalized cells. Similarly, if samples from non-immortalized cells harbor a nucleic acid sequence that immortalized cells lack, this nucleic acid sequence could be a marker for distinguishing immortalized cells from non-immortalized cells. Similar methods can elucidate polypeptide markers by utilizing polypeptide analytical techniques (e.g., PAGE, SDS-PAGE, procedures comprising antibodies, and HPLC techniques known in the art).

Identification of Totipotent Cells

Totipotent cells can be identified by a number of tests. Examples of these tests include:

(1) identifying a marker specific for totipotent cells;
(2) performing one or more nuclear transfer cycles with a cell (as described hereafter) and developing the resulting embryo into an animal.

Markers can be utilized to distinguish totipotent cells from non-totipotent cells. Markers can be selected from the group of low molecular weight markers, macromolecular markers, cell surface markers, and intracellular markers. Examples of markers that may be suitable for identifying totipotent cells can be selected from the group consisting of alkaline phosphatase, cytokeratin, vimentin, laminin, and c-kit. These markers are well known to a person of ordinary skill in the art and these examples are not meant to be limiting.

Some of these markers have been tested for cultured bovine cells being identified for totipotency. As noted previously, totipotent, immortalized bovine cells of the invention generally do not appreciably stain for alkaline phosphatase. Therefore the cells of the invention are to be contrasted with pluripotent cells discussed in previously referenced publications. It should be noted that some of the exemplary markers listed previously may not be specific for totipotent cells as some of these markers may exist in pluripotent cells as well as in totipotent cells. For example, although immortalized, totipotent bovine cells do not appreciably stain for alkaline phosphatase, immortalized, totipotent porcine cells may appreciably stain for alkaline phosphatase. The invention relates to any markers specific for totipotent cells that are known to a person of ordinary skill in the art.

Markers for totipotency that are not clearly defined in the art can be elucidated by processes defined in the previous section, which illustrates methods for elucidating immortalization cell markers.

A preferred test for determining totipotency of cells is determining whether cells give rise to totipotent embryos and eventually cloned animals. This test represents a definitive test for cellular totipotency. An example of such a test includes the following steps: (1) utilizing a potentially totipotent cell for nuclear transfer with an enucleated oocyte; (2) allowing the resulting cybrid to develop; (3) separating an embryo that developed from the cybrid into individual cells and subjecting one or more of the individual cells to a second round of nuclear transfer; (4) allowing a resulting cybrid from step (3) to develop into an embryo; (5) implanting the embryo from step (2) or (4) into a uterine environment; and (6) allowing the embryo to develop. If the ensuing fetus develops past the first trimester of pregnancy then the cells initially used for nuclear transfer are most likely totipotent cells. If the cells utilized for nuclear transfer develop into a live born cloned animal then the cells are definitively totipotent. Examples of the techniques utilized for this exemplary test (e.g., enucleation of oocytes and nuclear transfer) are described completely in the art and in exemplary embodiments defined hereafter.

Hence, the materials and methods provided herein are the first to feature immortalized, totipotent cells for cloning a bovine animal. As described above these materials and methods can be applied to other ungulates due to the high degree of nuclear DNA sequence homology among ungulates. Using the tests for identifying immortalized, totipotent cells, the methods and materials described herein can be modified by a person of ordinary skill in the art to produce immortalized, totipotent cells from any type of precursor cell. Hence, the invention covers any of the materials and methods described herein as well as modifications to these methods for generating immortalized, totipotent cells, since a person of ordinary skill in the art can readily produce immortalized, totipotent cells by utilizing the materials and methods described herein in conjunction with methods for identifying immortalized, totipotent cells.

II. Transgenic Immortalized and Totipotent Cells

Materials and methods readily available to a person of ordinary skill in the art can be utilized to convert immortalized, totipotent cells of the invention into transgenic immortalized, totipotent cells. Once the nuclear DNA is modified in the immortalized, totipotent cells of the invention, embryos and animals arising from these cells can also comprise the modified nuclear DNA. Hence, materials and methods readily available to a person of ordinary skill in the art can be applied to the immortalized, totipotent cells of the invention to produce transgenic animals and chimeric animals. See, e.g., EPO 264 166, entitled "Transgenic Animals Secreting Desired Proteins Into Milk"; WO 94/19935, entitled "Isolation of Components of Interest From Milk"; WO 93/22432, entitled "Method for Identifying Transgenic Pre-implantation Embryos"; and WO 95/17085, entitled "Transgenic Production of Antibodies in Milk," all of which are incorporated by reference herein in their entirety including all figures, drawings and tables.

Methods for generating transgenic cells typically include the steps of (1) assembling a suitable DNA construct useful for inserting a specific DNA sequence into the nuclear genome of a cell; (2) transfecting the DNA construct into the cells; (3) allowing random insertion and/or homologous recombination to occur. The modification resulting from this process may be the insertion of a suitable DNA construct(s) into the target genome; deletion of DNA from the target genome; and/or mutation of the target genome.

DNA constructs can comprise a gene of interest as well as a variety of elements including regulatory promoters, insulators, enhancers, and repressors as well as elements for ribosomal binding to the RNA transcribed from the DNA construct. DNA constructs can also encode ribozymes and anti-sense DNA and/or RNA, identified previously herein. These examples are well known to a person of ordinary skill in the art and are not meant to be limiting.

Due to the effective recombinant DNA techniques available in conjunction with DNA sequences for regulatory elements and genes readily available in data bases and the commercial sector, a person of ordinary skill in the art can readily generate a DNA construct appropriate for establishing transgenic cells using the materials and methods described herein.

Transfection techniques are well known to a person of ordinary skill in the art and materials and methods for carrying out transfection of DNA constructs into cells are commercially available. Materials typically used to transfect cells with DNA constructs are lipophilic compounds, such as Lipofectin™ for example. Particular lipophilic compounds can be induced to form liposomes for mediating transfection of the DNA construct into the cells.

Target sequences from the DNA construct can be inserted into specific regions of the nuclear genome by rational design of the DNA construct. These design techniques and methods are well known to a person of ordinary skill in the art. See, U.S. Pat. No. 5,633,067, "Method of Producing a Transgenic Bovine or Transgenic Bovine Embryo," DeBoer et al., issued May 27, 1997; U.S. Pat. No. 5,612,205, "Homologous Recombination in Mammalian Cells," Kay et al., issued Mar. 18, 1997; and PCT publication WO 93/22432, "Method for Identifying Transgenic Pre-Implantation Embryos," both of which are incorporated by reference herein in their entirety, including all figures, drawings, and tables. Once the desired DNA sequence is inserted into the nuclear genome, the location of the insertion region as well as the frequency with which the desired DNA sequence has inserted into the nuclear genome can be identified by methods well known to those skilled in the art.

Once the transgene is inserted into the nuclear genome of the immortalized, totipotent cell, that cell can be used as a nuclear donor for cloning a transgenic animal. A description of the embodiments related to transgenic animals are described in more detail hereafter.

A. Diseases and Parasites

Desired DNA sequences can be inserted into the (nuclear cellular) genome to enhance the resistance of a cloned transgenic animal to particular parasites and diseases. Examples of parasites include worms, flies, ticks, and fleas. Examples of infectious agents include bacteria, fungi, and viruses. Examples of diseases include Johne's, BVD, tuberculosis, foot and mouth, BLV, BSE and brucellosis. These examples are not limiting and the invention relates to any disease or parasite or infectious agent known in the art. See, e.g., *Hagan & Bruners Infectious Diesases of Domestic Animals* (7th edition), Gillespie & Timoney, copyright 1981, Cornell University Press, Ithaca N.Y.

A transgene can confer resistance to a particular parasite or disease by completely abrogating or partially alleviating the symptoms of the disease or parasitic condition, or by producing a protein which controls the parasite or disease.

B. Elements of DNA Constructs and Production of DNA Constructs

A wide variety of transcriptional and translational regulatory sequences may be employed, depending upon the nature of the host. The transcriptional and translational regulatory signals may be derived from viral sources, such as adenovirus, bovine papilloma virus, cytomegalovirus, simian virus, or the like, whereas the regulatory signals are associated with a particular gene sequence possessing potential for high levels of expression. Alternatively, promoters from mammalian expression products, such as actin, casein, alpha-lactalbumin, uroplakin, collagen, myosin, and the like, may be employed. Transcriptional regulatory signals may be selected which allow for repression or activation, so that expression of the gene product can be modulated. Of interest are regulatory signals which can be repressed or initiated by external factors such as chemicals or drugs. Other examples of regulatory elements are described herein.

C. Examples of Preferred Recombinant Products

A variety of proteins and polypeptides can be encoded by a gene harbored within a DNA construct suitable for creating transgenic cells. Those proteins or polypeptides include hormones, growth factors, enzymes, clotting factors, apolipoproteins, receptors, drugs, pharmaceuticals, bioceuticals, nutraceuticals, oncogenes, tumor antigens, tumor suppressors, cytokines, viral antigens, parasitic antigens, bacterial antigens and chemically synthesized polymers and polymers biosynthesized and/or modified by chemical, cellular and/or enzymatic processes. Specific examples of these compounds include proinsulin, insulin, growth hormone, androgen receptors, insulin-like growth factor I, insulin-like growth factor II, insulin growth factor binding proteins, epidermal growth factor, TGF-$\alpha$, TGF-$\beta$, dermal growth factor (PDGF), angiogenesis factors (acidic fibroblast growth factor, basic fibroblast growth factor and angiogenin), matrix proteins (Type IV collagen, Type VII collagen, laminin), oncogenes (ras, fos, myc, erb, src, sis, jun), E6 or E7 transforming sequence, p53 protein, cytokine receptor, IL-1, IL-6, IL-8, IL-2, $\alpha$, $\beta$, or $\gamma$IFN, GMCSF, GCSF, viral capsid protein, and proteins from viral, bacterial and parasitic organisms. Other specific proteins or polypeptides which can be expressed include: phenylalanine hydroxylase, $\alpha$-1-antitrypsin, cholesterol-7$\alpha$-hydroxylase, truncated apolipoprotein B, lipoprotein lipase, apolipoprotein E, apolipoprotein A1, LDL receptor, scavenger receptor for oxidized lipoproteins, molecular variants of each, VEGF, and combinations thereof. Other examples are clotting factors, apolipoproteins, drugs, tumor antigens, viral antigens, parasitic antigens, monoclonal antibodies, and bacterial antigens. One skilled in the art readily appreciates that these proteins belong to a wide variety of classes of proteins, and that other proteins within these classes can also be used. These are only examples and are not meant to be limiting in any way.

It should also be noted that the genetic material which is incorporated into the cells from DNA constructs includes (1) nucleic acid sequences not normally found in the cells; (2) nucleic acid molecules which are normally found in the cells but not expressed at physiological significant levels; (3) nucleic acid sequences normally found in the cells and normally expressed at physiological desired levels; (4) other nucleic acid sequences which can be modified for expression in cells; and (5) any combination of the above.

In addition, DNA constructs may become incorporated into the nuclear DNA of cells, where the incorporated DNA can be transcribed into ribonucleic acid molecules that can cleave other RNA molecules at specific regions. Ribonucleic acid molecules which can cleave RNA molecules are referred to in the art as ribozymes, which are RNA molecules themselves. Ribozymes can bind to discrete regions on a RNA molecule, and then specifically cleave a region within that binding region or adjacent to the binding region. Ribozyme techniques can thereby decrease the amount of polypeptide translated from formerly intact message RNA molecules.

Furthermore, DNA constructs can be incorporated into the nuclear complement of cells and when transcribed produce RNA that can bind to both specific RNA or DNA sequences. The nucleic acid sequences are utilized in anti-sense techniques, which bind to the message (mRNA) and block the translation of these messages. Anti-sense techniques can thereby block or partially block the synthesis of particular polypeptides in cells.

III. Nuclear Transfer

Nuclear transfer (NT) techniques using non-immortalized and non-totipotent cells are well known to a person of ordinary skill in the art. See, U.S. Pat. No. 4,994,384 (Prather et al.) and 5,057,420 (Massey et al.). All of the advantages inherent to using the immortalized, totipotent cells as described above are also advantages for NT techniques, specifically the fact that the immortalized, totipotent cells are a nearly unlimited source of nuclear donors and that these cells increase the efficiency of NT. Exemplary embodiments define a two-cycle NT technique that provides for efficient production of totipotent bovine embryos. This technique can be applied to any mammal, preferably ungulates.

A. Nuclear Donors

Immortalized, totipotent cells of the invention can be used as nuclear donors in a NT process for generating a cloned embryo. As described above, the immortalized, totipotent cells can be generated from nearly any type of cell. For NT techniques, a donor cell may be separated from a growing cell mass or isolated from a cell line. The entire cell may be placed in the perivitelline space of a recipient oocyte or may be directly injected into the recipient oocyte by aspirating the nuclear donor into a needle, placing the needle into the recipient oocyte, releasing the nuclear donor and removing the needle without significantly disrupting the plasma membrane of the oocyte. Alternatively, a nucleus (karyoplast) may be isolated from a nuclear donor and placed into the perivitelline space of or injected directly into the recipient oocyte, for example.

B. Recipient Oocytes

A recipient oocyte is typically an oocyte with a portion of its ooplasm removed, where the removed ooplasm comprises the oocyte nucleus. Enucleation techniques are well known to a person of ordinary skill in the art. See e.g., U.S. Pat. Nos. 4,994,384 and 5,057,420.

Oocytes can be isolated from either oviducts and/or ovaries of live animals by oviductal recovery procedures or transvaginal oocyte recovery procedures well known in the art and described herein. Furthermore, oocytes can be isolated from deceased animals. For example, ovaries can be obtained from abattoirs and the oocytes aspirated from these ovaries. The oocytes can also be isolated from the ovaries of a recently sacrificed animal or when the ovary has been frozen and/or thawed.

Oocytes can be matured in a variety of media well known to a person of ordinary skill in the art. One example of such a medium suitable for maturing oocytes is depicted in an exemplary embodiment described hereafter. Oocytes can be successfully matured in this type of medium within an environment comprising 5% $CO_2$ at 39° C. Oocytes may be cryopreserved and then thawed before placing the oocytes in maturation medium. Cryopreservation procedures for cells and embryos are well known in the art as discussed herein.

The nuclear donor may be incorporated into either a young or an aged oocyte. The age of the oocyte can be determined by the time that has elapsed since the oocyte was placed in maturation medium and the time it was activated. A young oocyte can be defined as an oocyte that is cultured in vitro less than 28 hours before activation. An aged oocyte is defined as an oocyte that is cultured in vitro for more than 28 hours before activation.

The age of the oocytes can be functionally identified by the appearance of their ooplasm. For example, because certain cellular materials have not yet dispersed within the ooplasm of a young oocyte, young oocytes have a pycnotic appearance. Aged oocytes, in comparison, are characterized by a more homogeneous cytoplasm. A publication discussing the use of aged oocytes for NT is WO 97/07662, entitled "Inactivated Oocytes as Cytoplast Recipients for Nuclear Transfer."

The nuclear donor cell and the recipient oocyte can arise from the same specie or different species. For example, a bovine immortalized, totipotent cell can be inserted into a bovine enucleated oocyte. Alternatively, an immortalized, totipotent cell derived from a bison can be inserted into a bovine enucleated oocyte. Any nuclear donor/recipient oocyte combinations are envisioned by the invention. Preferably the nuclear donor and recipient oocyte arise from one specie or different species of ungulates. Cross-species NT techniques can be utilized to produce cloned animals that are endangered.

The oocytes can be activated by electrical and/or non-electrical means before, during, and/or after fusion of the nuclear donor and recipient oocyte. For example, the oocyte can be placed in a medium containing one or more components suitable for non-electrical activation prior to fusion. Alternatively, a fused cybrid can be placed in a medium containing one or more components suitable for non-electrical activation. The activation process is discussed in greater detail hereafter.

C. Injection/Fusion

A nuclear donor can be translocated into an oocyte using a variety of materials and methods that are well known to a person of ordinary skill in the art. In one example, a nuclear donor may be directly injected into a recipient oocyte. This direct injection can be accomplished by gently pulling a nuclear donor into a needle, piercing a recipient oocyte with that needle, releasing the nuclear donor into the oocyte, and removing the needle from the oocyte without significantly disrupting its membrane. Appropriate needles can be fashioned from glass capillary tubes, as defined in the art and specifically by publications incorporated herein by reference.

In another example, at least a portion of plasma membrane from a nuclear donor and recipient oocyte can be fused together using techniques well known to a person of ordinary skill in the art. See, Willadsen, 1986, *Nature* 320:63–65, hereby incorporated herein by reference in its entirety including all figures, tables, and drawings. Typically, lipid membranes can be fused together by electrical and chemical means, as defined previously and in other references incorporated by reference herein.

Other examples of non-electrical means of cell fusion involve incubating cybrids in solutions comprising polyethylene glycol (PEG), and/or Sendai virus. Various molecular weights of PEG can be utilized for cell fusion.

Although the efficiency of NT as a process is sensitive to minor modifications, other variables for fusion can be determined without undue experimentation. For example, modifications to cell fusion techniques can be monitored for their efficiency by viewing the degree of cell fusion under a microscope. The resulting embryo can then be cloned and identified as a totipotent embryo by the same methods as those previously described herein for identifying immortalized, totipotent cells, which can include tests for selectable markers and/or tests for developing an animal.

D. Activation

Methods of activating oocytes and cybrids are known to those of ordinary skill in the art. See, U.S. Pat. No. 5,496,720, "Parthenogenic Oocyte Activation," Susko-Parrish et al., issued on Mar. 5, 1996, hereby incorporated by reference herein in its entirety including all figures, tables, and drawings.

Both electrical and non-electrical means can be used for activating the cybrids. Although use of a non-electrical means for activation is not always necessary, non-electrical activation can enhance the developmental potential of cybrids, particularly when young oocytes are utilized as recipients.

Examples of electrical techniques for activating cells are well known in the art. See, U.S. Pat. Nos. 4,994,384 and 5,057,420. Non-electrical means for activating cells can include any method known in the art that increases the probability of cell division. Examples of non-electrical means for activating a nuclear donor and/or recipient can be accomplished by introducing cells to ethanol; inositol tris-phosphate (IP$_3$); Ca$^{++}$ ionophore and protein kinase inhibitors such as 6-dimethylaminopurine; temperature change; protein synthesis inhibitors (e.g., cyclohexamide); phorbol esters such as phorbol 12-myristate 13-acetate (PMA); mechanical techniques, thapsigargin, and sperm factors. Sperm factors can include any component of a sperm. Other non-electrical methods for activation include subjecting the cell or cells to cold shock and/or mechanical stress.

Examples of preferred protein kinase inhibitors are protein kinase A, G, and C inhibitors such as 6-dimethylaminopurine (DMAP), staurosporin, 2-aminopurine, sphingosine. Potentially, tyrosine kinase inhibitors may also be utilized to activate cells.

Although the NT process is sensitive to minor modifications, other variables for activation can be determined without undue experimentation. Other activation materials and methods can be identified by modifying the specified conditions defined in the exemplary protocols described hereafter and in U.S. Pat. No. 5,496,720.

The result of any modifications upon efficiency and totipotency of the activated embryo can be identified by the methods described previously in the section entitled "Identification of Immortalized and Totipotent Cells." Methods for identifying totipotent embryos can include one or more tests, such as (a) identifying specific markers for totipotent cells in embryos, and (b) by determining whether the embryos are totipotent by allowing them to develop into an animal. Therefore, the invention relates to any modifications to the activation procedures described herein even though these modifications may not be explicitly stated herein.

F. Manipulation of Embryos Resulting from Nuclear Transfer

An embryo resulting from a NT can be manipulated in a variety of manners. The invention relates to cloned embryos that arise from at least one NT.

Exemplary embodiments of the invention demonstrate that two or more NT procedures may enhance the efficiency for the production of totipotent embryos. The exemplary embodiments indicate that incorporating two or more NT procedures into methods for producing cloned totipotent embryos may enhance placental development. In addition, increasing the number of NT cycles involved in a process for producing totipotent embryos may represent a necessary factor for converting non-totipotent cells into totipotent cells. The effect of incorporating two or more NT cycles on the totipotency of resulting embryos is a surprising result, which was not previously identified or explored in the art.

Incorporating two or more NT cycles into methods for cloned totipotent embryos can provide another advantage. Incorporation of multiple NT procedures into methods for creating cloned totipotent embryos provides a method for multiplying the number of cloned totipotent embryos.

When multiple NT procedures are utilized for the formation of a cloned totipotent embryo, young or aged oocytes can be utilized as recipients in the first, second or subsequent NT procedures. For example, if a first NT and then a second NT are performed, the first NT can utilize a young enucleated oocyte as a recipient and the second NT may utilize an aged enucleated oocyte as a recipient. Alternatively, the first NT may utilize an aged enucleated oocyte as a recipient and the second NT may utilize a young enucleated oocyte as a recipient for the same two-cycle model for NT. In addition, both NT cycles may utilize young enucleated oocytes as recipients or both NT cycles may utilize aged enucleated oocytes as recipients in the two-cycle NT example.

For NT techniques that incorporate two or more NT cycles, one or more of the NT cycles may be preceded, followed, and/or carried out simultaneously with an activation step. As defined previously herein, an activation step may be accomplished by electrical and/or non-electrical means as defined herein. Exemplified embodiments described hereafter describe NT techniques that incorporate an activation step after one of the NT cycles. However, activation steps may also be carried out in conjunction with NT cycles (e.g., simultaneously with the NT cycle) and/or activation steps may be carried out prior to a NT cycle.

A preferred embodiment of the invention, for example, relates to a first NT utilizing a young enucleated oocyte as a recipient followed by activation. This, in turn, is followed by a second NT utilizing an aged enucleated oocyte as a recipient. This second NT procedure is not followed by activation. This example is not meant to be limiting and the invention relates to any number of NT cycles that are optionally preceded by, followed by, simultaneously carried out with an activation procedure.

NT techniques may utilize virtually any cell as a nuclear donor. For example, in a preferred embodiment, a first NT may utilize an immortalized, totipotent cell of the invention as a nuclear donor and a second NT may utilize an embryonic cell as a nuclear donor. The second NT cycle in this example may utilize a blastomere (a cell isolated from an embryo), a cell isolated from a fetus (e.g., a primordial germ cell) as a nuclear donor, a cell isolated from a cell line, or a synchronized cell (described herein). The invention pertains in part to utilizing nearly any type of cell as a nuclear donor in any NT. The effect of using different nuclear donors on the overall efficiency for producing cloned totipotent embryos can be tested by practicing the tests for totipotency described in the preceding section entitled "Identification of Immortalized and Totipotent Cells."

The cloned totipotent embryos resulting from NTs can be (1) disaggregated or (2) allowed to develop further.

If the embryos are disaggregated, these embryonic derived cells can be utilized to establish cultured cells. Any type of embryonic cell can be utilized to produce cultured cells. These cultured cells are sometimes referred to as embryonic stem cells or embryonic stem-like cells in the scientific literature. The embryonic stem cells can be derived from early embryos, morulae, and blastocyst stage embryos. Multiple methods are known to a person of ordinary skill in the art for producing cultured embryonic cells. These methods are enumerated in specific references previously incorporated by reference herein.

If the embryos are allowed to develop in utero, cells isolated from the developing fetus can be utilized to produce cultured cells. In preferred embodiments, primordial germ cells are isolated from the genital ridge of 28 to 75 day old developing cell masses for the establishment of cell lines. These cultured cells are sometimes referred to as embryonic germ cells (EG). These cultured cells can be generated using methods well known to a person of ordinary skill in the art. The methods are enumerated in references previously incorporated by reference herein.

The cloned totipotent embryos resulting from NT can also be manipulated by cryopreserving and/or thawing the embryos. See, U.S. Pat. No. 5,160,312, entitled "Cryopreservation Process for Direct Transfer of Embryos," Voelkel, and issued on Nov. 3, 1992; and U.S. Pat. No. 4,227,381, entitled "Wind Tunnel Freezer," Sullivan et al., issued on Oct. 14, 1980, all of which are hereby incorporated by reference herein in their entireties including all tables, figures, and drawings. Other embryo manipulation methods include culturing, performing embryo transfer, dissociating for NT, dissociating for establishing cell lines for use in NT, splitting, aggregating, sexing, and biopsying the embryos resulting from NT, which are described hereafter. The exemplary manipulation procedures are not meant to be limiting and the invention relates to any embryo manipulation procedure known to a person of ordinary skill in the art.

IV. Development of Cloned Embryos

A. Totipotency

Totipotent embryos can be identified by the methods described in the section "Identification of Immortalized and Totipotent Cells." Individual cells can be isolated and subjected to these similar tests. The tests relate to similar markers for identifying totipotent cells, as well as a test for determining totipotency by allowing an embryo to develop until it passes the second trimester of gestation, or preferably, gives rise to a live born animal. Methods for identifying other markers for totipotency are also described in that section.

B. Culture of Embryos in vitro

Methods for culturing embryos in vitro are well known to those skilled in the art. See, U.S. Pat. No. 5,213,979, entitled "In vitro Culture of Bovine Embryos," First et al., issued on May 25, 1993, and U.S. Pat. No. 5,096,822, entitled "Bovine Embryo Medium," Rosenkrans, Jr. et al., issued on Mar. 17, 1992, both of which are incorporated by reference herein in its entirety, including all figures, tables, and drawings. In addition, exemplary embodiments for media suitable for culturing cloned embryos in vitro are described hereafter. Feeder cell layers may or may not be utilized for culturing cloned embryos in vitro. Feeder cells are described previously and in exemplary embodiments hereafter.

The present invention is superior to existing materials and methods for cloning organisms, because embodiments of the invention allow for culturing all cells and embryos in vitro prior to implantation. For example, cloning methods described for cloning ovine organisms require an in vivo development step in the oviducts of an ovine host animal before the embryos are implanted in a suitable host. Because embodiments of the present invention do not require in vivo development steps prior to implantation into the uterus, the materials and methods of the present invention represent an inventive step over cloning methods previously described by others.

C. Development of Embryos in utero

Cloned embryos can be cultured in an artificial or natural uterine environment after NT procedures. Examples of artificial development environments are being developed and some are known to those skilled in the art. Components of the artificial environment can be modified with little experimentation, for example, by modifying one component and monitoring the growth rate of the embryo.

Methods for implanting embryos into the uterus of an animal are also well known in the art. Preferably, the developmental stage of the embryo(s) is correlated with the estrus cycle of the animal.

Embryos from one specie can be placed into the uterine environment of an animal from another specie. For example it has been shown in the art that bovine embryos can develop in the oviducts of sheep. Stice & Keefer, 1993, "Multiple generational bovine embryo cloning," *Biology of Reproduction* 48: 715–719. The invention relates to any combination of ungulate embryo in any other ungulate uterine environment. The cross-species relationship between embryo and uterus can allow for efficient production of cloned animals of an endangered species. For example, a bison embryo can develop in the uterus of a domestic bovine. In another example, a big-horn sheep embryo can develop in the uterus of a large domesticated sheep.

Once the embryo is placed in the uterus of an animal, the embryo can develop to term. Alternatively, the embryo can be allowed to develop in the uterus and then can be removed at a chosen time. Surgical methods are well known in the art for removing fetuses from uteri before they are born.

V. Cloned Animals

A. Bovine Cloned Animals

As described previously herein, the invention provides the advantages of being able to assess the phenotype of an animal before cloning. This is an advantage of the invention since previous reports have only allowed the cloning of bovine animals from blastomeres, a method that does not allow for phenotype assessment.

Multiple products can be isolated from a cloned animal. For example, semen can be collected from an animal, such as a bovine bull. Semen can be cryopreserved as well as separated sperm into sex-specific fractions. See, U.S. Pat. Nos. 5,439,362, 5,346,990, and 5,021,244, entitled "Sex-associated Membrane Proteins and Methods for Increasing the Probability that Offspring Will be of a Desired Sex," Spaulding, and issued on Aug. 8, 1995, Sep. 13, 1994, and Jun. 4, 1991, respectively, all of which are hereby incorporated by reference herein in their entireties including all figures, drawings, and tables. Methods of collecting semen are well known to a person of ordinary skill in the art. *Physiology of Reproduction and Artificial Insemination of Cattle* (2nd. edition), Salisbury et al., copyright 1961, 1978, W. H. Freeman & Co., San Francisco.

The invention relates in part to any products collected from a cloned animal, preferably a cloned bovine animal. The products can be any body fluids or organs isolated from the animal, or any products isolated from the fluids or organs. In preferred embodiments, products such as milk and meat may be collected from cloned animals, preferably cloned bovine animals. In another embodiment, the invention relates to determining the phenotype of a bovine steer, which is a neutered animal, and then cloning this animal such that the cloned animals are reproductively functional and can be used to produce semen. Other preferred embodiments of the invention relate to such products as xenograft materials, sperm, embryos, oocytes, any type of cells, and offspring harvested from cloned animals of the invention, preferably cloned bovine animals.

Xenograft materials, which are described previously herein, can relate to any cellular material extracted from one organism and placed into another organism. Medical procedures for extracting the cellular material from one organism and grafting it into another organism are well known to a person of ordinary skill in the art. Examples of preferable xenograft cellular materials can be selected from the group consisting of liver, lung, heart, nerve, gallbladder, and pancreas cellular material.

B. Non-Bovine Cloned Animals

Due to the high DNA sequence homology between bovine animals and other ungulates, the materials and methods of the invention can be utilized to clone other ungulates. The materials and methods of the invention are the most efficient means for cloning a mammal as known in the state of the art.

In preferred embodiments the materials and methods of the invention can be utilized to clone endangered species, such as bison. In addition, the materials and methods of the invention can be utilized to clone commercially relevant ungulates, such as pigs. Due to the methods for reprogramming primary cells isolated from an animal into immortalized, totipotent cells, the more closely related the animal species is to cattle, the higher probability that the cloning methods of the invention will have greater success. Exemplary embodiments are described hereafter for cloning non-bovine animals.

C. Cloned Animals with Modified Nuclear DNA

As discussed in a previous section, transgenic animals can be generated from the methods of the invention by using transgenic techniques well known to those of ordinary skill in the art. Preferably, cloned transgenic bovine animals are produced from these methods. These cloned transgenic animals can be engineered such that they are resistant or partially resistant to diseases and parasites endemic to such animals. Examples of these diseases and parasites are outlined in a preceding section.

Moreover, the cloned transgenic animals can be engineered such that they produce a recombinant product. Examples of recombinant products are outlined in a preceding section. The expression of these products can be directed to particular cells or regions within the cloned transgenic animals by selectively engineering a suitable promoter element and other regulatory elements to achieve this end.

For example, human recombinant products can be expressed in the urine of cattle by operably linking a uroplakin promoter to the DNA sequence encoding a recombinant product. Alternatively, examples are well known to a person of ordinary skill in the art for selectively expressing human recombinant products in the milk of a bovine animal.

Once the recombinant product or products have been expressed in a particular tissue or fluid of the cloned transgenic animal, the suitable tissue or fluid can be collected using methods well known in the art. Recombinant products can be purified from that fluid or tissue by using standard purification techniques well known to a person of ordinary skill in the art.

EXAMPLES

The examples below are non-limiting and are merely representative of various aspects and features of the present invention.

Example 1

Feeder Layer Preparation

A feeder cell layer was prepared from mouse fetuses that were from 10 to 20 days gestation. The head, liver, heart and alimentary tract were removed and the remaining tissue washed and incubated at 37° C. in 0.025% trypsin-0.02%, EDTA (Difco, Cat #0153-61-1). Loose cells were cultured in tissue culture dishes containing MEM-alpha supplemented with penicillin, streptomycin, 10% fetal calf serum and 01 mM 2-mercaptoethanol. The feeder cell cultures were established over a two to three week period at 37.4° C., 3.5% $CO_2$ and humidified air. Before being used as feeder cells, mouse fibroblasts were pre-treated with mitomycin C (Calbiochem, Cat #47589) at a final concentration of 10 μg/ml for 3 hours and washed 5 times with PBS before pre-equilibrated growth media was added.

Feeder cells can be established from bovine fetuses from 30 to 70 days using the same procedure. Bovine fetal cells may be optionally treated with mitomycin C.

Example 2

Establishing Cultured Cells From Non-Embryonic Tissue

One advantage provided by the materials and methods defined herein is the ability to create an immortalized and totipotent cell from virtually any type of precursor cell. These precursor cells can be embryonic cells, cultured embryonic cells, primordial germ cells, fetal cells, and cells isolated from the tissues of adult animals, for example. Cells isolated from the kidney and ear of an adult grown bovine have been utilized as precursor cells for the generation of immortalized, totipotent cells.

After cells are isolated from their respective tissues, the cells can be subjected to the materials and methods defined in Example 3.

A first step towards generating immortalized, totipotent cells from tissues of grown animals includes a primary culture of isolated cells. A protocol for culturing cells isolated from the tissues of grown animals is provided hereafter. Although the illustrative protocol relates to ear punch samples, this protocol can apply to cells isolated from any type of tissue.

The following steps are preferably performed utilizing sterile procedures:

1) Wash each ear sample twice with 2 mL of trypsin/EDTA solution in two separate 35 mm Petri dishes. Process each ear sample separately. Mince the ear sample with sterile scissors and scalpel in a 35 mm Petri dish containing 2 mL of trypsin/EDTA solution. The minced pieces are preferably less than 1 mm in diameter.
2) Incubate minced ear pieces in the trypsin/EDTA solution for 40–50 min. in a 37° C. incubator with occasional swirling. The trypsin/EDTA solution is described in more detail hereafter. The dish may be wrapped with a stretchable material, such as Parafilm®, to reduce $CO_2$ accumulation.
3) Transfer digested ear pieces to a 15 mL sterile tube. Wash the dish from which the digested ear pieces were recovered with 2 mL of the trypsin/EDTA solution and transfer this wash solution to the sterile tube.
4) Vortex the tube at high speed for 2 min.
5) Add 5 mL of media (defined below) to inactivate the trypsin.
6) Centrifuge the 15 mL tube at 280 xg for 10 minutes.
7) Decant the supernatant and re-suspend the cell pellet in residual solution by gently taping the side of the tube.
8) Add 2 mL of media to the tube and then centrifuge as described in step (6).
9) Decant the supernatant, re-suspend the pellet as described in step (7), then add 2 mL of media.
10) Keep 2–3 pieces of the ear for DNA analysis and store at −20° C. in a 15 mL tube.
11) Transfer resuspended cells into a 35 mm Nunc culture dish and incubate at 37° C. in a humidified 5% $CO_2$/95% air atmosphere.
12) Change media every 2 days.

Trypsin/EDTA solution:

0.025% trypsin (w/v) (Bacto trypsin, Difco #cat 0153-61-1)

0.02% EDTA (Sigma) (w/v)
Add the trypsin and EDTA to Ca$^{2+}$-free and Mg$^{2+}$-free Dulbecco's phosphate-buffered saline (PBS) (Gibco cat# 450-1600EA) and sterilize by filtration through a 0.2 μm filter.
Media:
Combine Alpha minimum essential medium (MEM) (Biowhittaker) with 10% fetal bovine serum (Hyclone), 4 mM L-glutamine, 100 U/mL penicillin, 100 μg/mL streptomycin, 0.25 μg/mL amphotercin B (Fungizone).

This protocol has been also successfully utilized to establish cultures of kidney and liver cells isolated from grown bovine animals. As discussed above, the protocol can be utilized to create cell cultures from any type of cell isolated from a grown animal, for any species or family of animals.

Example 3

Figure 2:
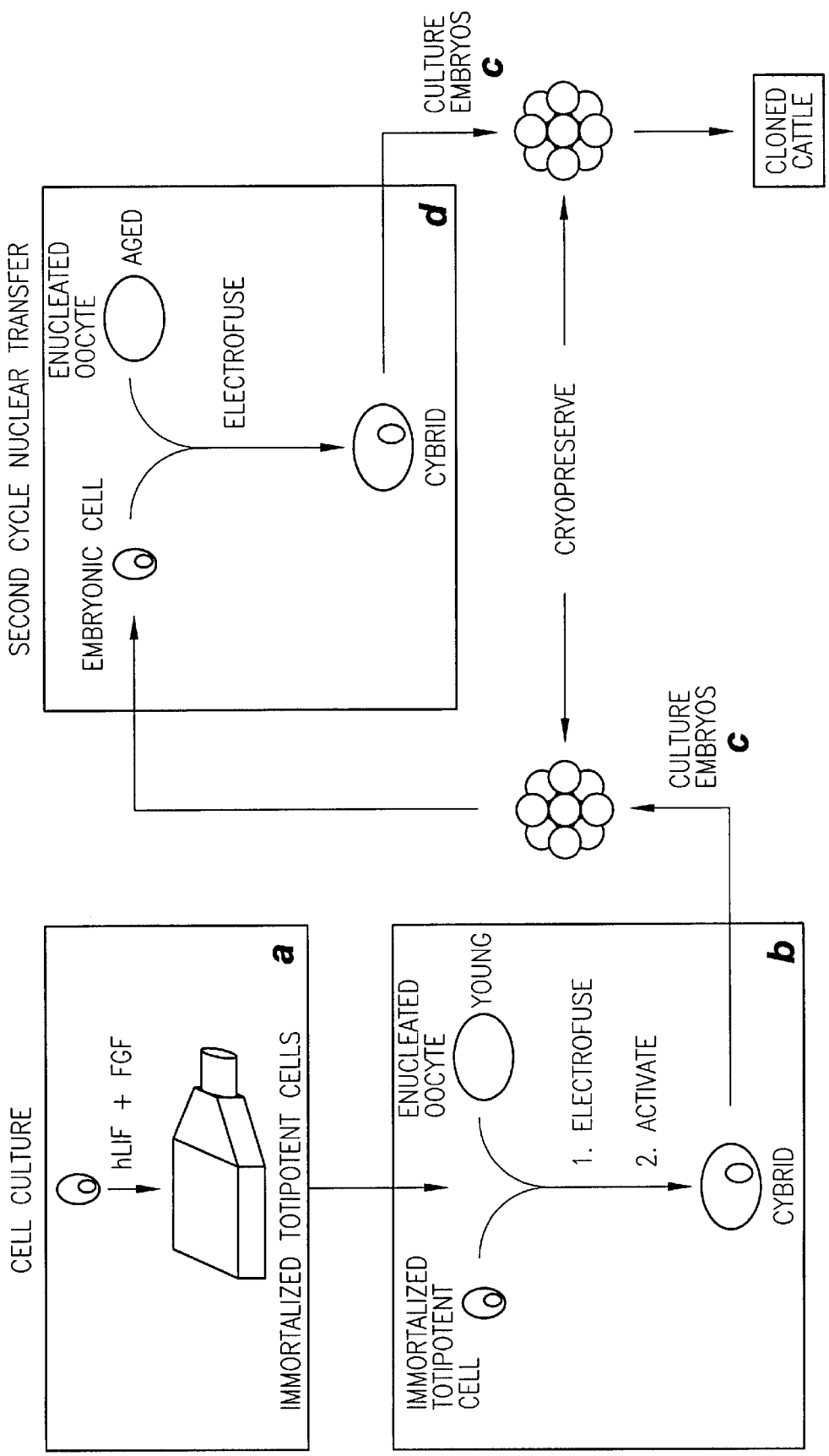
FIG. 2 illustrates an embodiment of the invention related to cloning. The figure illustrates a cloning procedure in which (a) a precursor cell is reprogrammed into an immortalized, totipotent cell; (b) the immortalized, totipotent cell is utilized as a donor for a first nuclear transfer, which utilizes a young oocyte; (c) the embryo arising from the first nuclear transfer is cultured; (d) a cell isolated from the embryo arising from the first nuclear transfer is utilized as a nuclear donor for a second nuclear transfer, which utilizes an aged oocyte; and (e) the embryo resulting from the second nuclear transfer may be cultured and then allowed to develop into a live born animal. The embryos resulting from the nuclear transfers may be cultured and/or cryopreserved and thawed.

Reprogramming and Establishment of Immortalized and Totipotent Cells from Precursor Cells The reprogramming procedures described hereafter can utilize any cell type of cells as precursor cells for the generation of immortalized, totipotent cells. As an example, the cell cultures described previously can be utilized as precursor cells for the reprogramming procedures described below. As another example, the following procedure describes one embodiment of the invention, where primordial germ cells were utilized as precursor cells for the generation of immortalized, totipotent cells. An embodiment of the reprogramming process is illustrated in FIG. 2.

A bovine fetus approximately 40 days old was obtained from a pregnant animal. The genital ridges were located at the caudo-ventral part of the abdominal cavity. Genital ridges were removed aseptically and washed in phosphate buffered saline (PBS) (Gibco, Cat #14287-015) with 500 U/mL penicillin/500 μg/ml streptomycin. The tissue was sliced into 1–1.5 mm pieces and placed into a solution containing pronase E (3mg/ml; Sigma Cat # P6911) in Tyrodes Lactate (TL) HEPES (Biowhittaker, Cat #04-616F) for 30–45 minutes at 35–37° C. The proteolytic action of pronase E disaggregated the slices of genital ridges to a cell suspension. Pronase E was removed by dilution and centrifugation in TL HEPES solution. After this step, the cell suspension was frozen and stored at −196° C.

A thawed cell suspension (final concentration 100,000 cells/ml) was placed into a 35 mm Petri dish containing a murine primary embryonic fibroblast feeder layer. The culture media used was MEM alpha (Biowhittaker, Cat #12-169F) supplemented with 0.1 mM 2-mercaptoethanol (Gibco, Cat #21985-023), 4 mM glutamine, 100 ng/ml human recombinant leukemia inhibitory factor (hrLIF; R&D System, Cat #250-L), 100 ng/ml bovine basic fibroblast growth factor (bFGF; R&D System, Cat #133-FB) and 10% fetal calf serum (FCS, HyClone, Cat #A1111D) at 37.5° C. and 3.5% CO$_2$. Exogenous steel factor (e.g., membrane associated steel factor and soluble steel factor) was not added to the culture media. After 24 hours, and again at 48 hour intervals, supplemented culture media was replaced. After an initial culture of 6 days, concentrations of hrLIF and bFGF were lowered to 40 ng/ml, respectively. After nine days in culture, hrLIF and bFGF were removed from the medium entirely.

At the beginning of in vitro culture of genital ridge cells, simple embryonic bodies were occasionally observed. These bodies eventually disappeared with subsequent passages. The rate of establishing immortalized, totipotent cell lines from genital ridge cells was 100% and did not appear to be sex dependent. Table 1 contains data from establishment of seven immortalized, totipotent cell lines. Established immortalized, totipotent cell lines were maintained in MEM-alpha supplemented with 10% FCS which was replaced every second or third day. High density population cells were passaged every week at a dilution ratio of 1:4 to 1:8. Cells were passaged by incubating with 0.025% trypsin—0.02% EDTA mixture and preparing new cultures in fresh growth medium. The growth promoting capacity of MEM-alpha media for immortalized, totipotent cells was enhanced by adding insulin-transferrin, sodium selenite supplement, diluted to 1:100 (Sigma Cat #11884). As a preventive measure against mycoplasma contamination, short term cultivation with tylosine tartrate (Sigma, Cat T3151) was carried out. Before NT, cell lines were tested for presence of mycoplasma by PCR performed with DNA primers specific for mycoplasma sequences (Stratagene, Cat 302007).

TABLE 1

Characterization of Established Bovine Immortalized and Totipotent Cell Lines

| Cell line | Weight of fetus (gm) | Days in culture | Sex of Cell line |
|---|---|---|---|
| EG | 14.2 | >400 | male |
| EG-1 | 20.2 | >300 | male |
| EG-2 | 3.9 | >30 | female |
| EG-3 | 4.8 | >30 | male |
| EG-4 | 39.6 | >100 | female |
| EG-5 | 3.9 | >250 | male |
| EG-6 | 8.6 | >30 | male |

Example 4

Embryo Construction

The following embodiment of the invention describes materials and methods utilized to produce totipotent embryos of the invention. Immortalized embryos of the invention can be produced by utilizing immortalized and totipotent cells of the invention as nuclear donors in NT procedures. As described previously, multiple NT procedures can be utilized to create a totipotent embryo. The following two examples describe a multiple NT procedure, which describes the use of two NTs.

Mycoplasma free immortalized, totipotent cells used in the NT procedure, were prepared by cutting out a group of immortalized, totipotent cells from the feeder layer using a glass needle. The isolated immortalized, totipotent cells were then incubated in a TL HEPES solution containing from 1 to 3 mg/ml pronase E at approximately 32° C. for 1 to 4 hours, the amount of time which was needed in this example to disaggregate the cells. Once the cells were in a single cell suspension they were used for NT within a 2–3 hour period.

Oocytes aspirated from ovaries were matured overnight (16 hours) in maturation medium. Medium 199 (Biowhittaker, Cat #12-119F) supplemented with luteinizing hormone 10 IU/ml (LH; Sigma, Cat #L9773), 1 mg/ml estradiol (Sigma, Cat #E8875) and 10% FCS or estrus cow serum, was used. Within 16 hours of maturation, the cumulus layer expanded and the first polar bodies were extruded.

In the first NT procedure, young oocytes were stripped of their cumulus cell layers and nuclear material stained with Hoechst 33342 5mg/ml (Sigma, Cat #2261) in TL HEPES solution supplemented with cytochalasin B (7 μg/ml, Sigma, Cat #C6762) for 15 min. Oocytes were then enucleated in TL HEPES solution under mineral oil. A single immortalized, totipotent cell of optimal size (12 to 15 μm) was then inserted from a cell suspension and injected into the perivitelline space of the enucleated oocyte. The immortalized, totipotent cell and oocyte membranes were then induced to fuse by electrofusion in a 500 μm chamber by application of an electrical pulse of 90V for 15 μs.

Cybrid activation was induced by a 4 min exposure to 5 μM calcium ionophore A23187 (Sigma Cat. #C-7522) or ionomycin Ca-salt in HECM (hamster embryo culture medium) containing 1 mg/ml BSA followed by a 1:1000 dilution in HECM containing 30 mg/ml BSA for 5 min. For HECM medium, see, e.g., Seshagiri & Barister, 1989, "Phosphate is required for inhibition of glucose of development of hamster eight-cell embryos in vitro," *Biol Reprod.* 40: 599–606. This step is followed by incubation in CR2 medium containing 1.9 mM 6-dimethylaminopurine (DMAP; Sigma product, Cat # D2629) for 4 hrs followed by a wash in HECM and then cultured in CR2 media with BSA (3 mg/ml) under humidified air with 5% $CO_2$ at 39° C. For CR2 medium, see, e.g., Rosenkrans & First, 1994, "Effect of free amino acids and vitamins on cleavage and developmental rate of bovine zygotes in vitro," *J. Anim. Sci.* 72: 434–437. Mitotic divisions of the cybrid formed an embryo. Three days later the embryos were transferred to CR2 media containing 10% FCS for the remainder of their in vitro culture.

Table 2 shows the effect of oocyte age on blastocyst development. The data was obtained utilizing blastomeres from in vitro produced embryos or immortalized, totipotent cells as donor nuclei in the NT procedure. Developmental potential was measured in young versus aged oocytes.

TABLE 2

Effect of Oocyte Timing for Different Cell Sources

| oocyte age (hours) | Immortalized and Totipotent Cells (n = 174) | Blastomeres (n = 192) |
|---|---|---|
| 16–28 (n = 175) | 17.9% blastocyst (n = 140) | no development (n = 35) |
| 28–48 (n = 191) | no development (n = 34) | 17.3% blastocyst (n = 157) |

The data presented in Table 2 shows that oocytes maintained in culture for 16–28 h were more suitable recipients for immortalized, totipotent cells, while aged oocytes maintained in culture for 28–48 h were a more suitable recipient for blastomeres derived from embryos. In addition, activation procedures differed between young and aged oocytes. Young oocytes, when used in the NT procedure, appear to require chemical activation with ionomycin and DMAP from these studies. Aged oocytes, on the other hand, appear to be easily activated by electrofusion according to these studies.

Example 5

Second Nuclear Transfer (Recloning)

Cells obtained from fetuses and embryos produced by the NT procedures described herein can be used in a second NT, or recloning, procedure. For example, a fetus can be harvested from a maternal host, the head, vicera, and genital ridge removed, and the remaining fetal cells used to establish a cell line to provide nuclear donor material for a subsequent NT procedure. The following example describes obtaining and using a blastomere from an NT embryo as a nuclear donor in a recloning procedure.

Embryos from the first generation NT at the morula stage were disaggregated either by pronase E (1–3 mg/ml in TL HEPES) or mechanically after treatment with cytochalasin B. Single blastomeres were placed into the perivitelline space of enucleated aged oocytes (28–48 hours of incubation). Aged oocytes were produced by incubating matured "young" oocytes for an additional time in CR2 media with 3 mg/ml BSA in humidified air with 5% $CO_2$ at 39° C.

A blastomere from an embryo produced from an immortalized, totipotent cell was fused into the enucleated oocyte via electrofusion in a 500 μm chamber with an electrical pulse of 105V for 15 μs in an isotonic sorbitol solution (0.25 M) at 30° C. Aged oocytes were simultaneously activated with a fusion pulse, not by chemical activation as with young oocytes.

After blastomere-oocyte fusion, the cybrids from second generation NT were cultured in CR2 media supplemented with BSA (3 mg/ml) under humidified air with 5% $CO_2$ at 39° C. On the third day of culture, developing embryos were evaluated and cultured further until day seven in CR2 media containing 10% FCS. Morphologically good to fair quality embryos were non-surgically transferred into recipient females. Table 3 shows the increased gestation length achieved by use of recloned (double NT) immortalized, totipotent cells.

TABLE 3

Development of Immortalized and Totipotent Cells Derived Fetuses after Double NT

| | No. of embryos transferred | No. of recipients transferred into | No. of pregnant recipients after 140 days | No. of calves |
|---|---|---|---|---|
| Exper #1 | 15 | 5 | 1 | 1 |
| Exper #2 | 18 | 6 | 1 (two fetuses) | 2 |

Example 6

Cloning Non-Bovine Ungulates

The specification provides for methods of cloning non-bovine ungulates. Examples of such ungulates can be selected from the group consisting of bovids, ovids, cervids, suids, equids and camclids, such as bison, sheep, big-horn sheep, caribou, antelope, deer, goat, water buffalo, camel, and pig.

Immortalized, totipotent cell lines can be prepared from multiple types of cells isolated from the non-bovine ungulate by using the methods described in previous examples relating to bovine animals, or by using the screening procedures for these methods as described in the specification. Virtually any type of cell isolated from the non-bovine ungulate can be utilized to establish an immortalized, totipotent cell line. For example, an ear-punch sample taken from a bison can be cultured in vitro using a variety of cell culture media such as MEM-alpha medium.

Bison-derived primary cells can then be converted or reprogrammed into immortalized, totipotent bison cells by supplementing the cell culture medium with hrLIF and bFGF as described in previous examples and in the specification. Alternatively, the bison-derived primary cells can be converted into immortalized, totipotent cells by supplementing the growth medium with other types of molecules identified by methods for identifying such reprogramming molecules as described in the specification. The reprogrammed bison-derived cells can then be tested for totipotency by analyzing selected markers, such as alkaline phosphatase, laminin, and c-kit. In addition, the bison-derived cells can be considered permanent if the number of cell divisions exceeds the Hayflick limit and/or if the cells can grow to confluency after being replated under conditions where the cells are not in physical contact with one another, for example.

Once totipotent, immortalized cells have been established as nuclear donors, proper enucleated oocytes can be prepared for NT. Oocytes from the same or different specie as the nuclear donor can be used for NT. For example, a bison-derived nuclear donor cell can be fused or directly injected into a bison-derived enucleated oocyte or an enucleated oocyte from another specie, such as a bovine.

As described in the specification, the oocytes can be derived from any ungulate in a variety of ways, such as sacrificing an animal and retrieving oocytes from its oviducts, or spaying the animals by ovarian hysterectomy and isolating the oocytes from the oviducts or ovaries. Oocytes can also be obtained from live animals by utilizing such methods as transvaginal oocyte recovery. The oocytes can then be enucleated by using methods described herein as applied to sheep or cattle. These methods can be easily applied to oocytes derived from other ungulates.

Nuclear transfer techniques can be preformed after enucleated oocytes and nuclear donor cells are prepared. Young or aged oocytes can be utilized for the NT procedure, and the number of NTs can vary as described in the specification. In addition the parameters that define the fusion step for a NT may be varied as described herein. An activation step can be applied to one or more of the NT cycles. For example, the NT cycles defined in a previous exemplary embodiment can be applied to the generation of cloned bison. The embryo resulting from the NT can be tested for totipotency by utilizing tests for one or more markers, such as alkaline phosphatase, cytokeratin, vimentin, laminin, and c-kit. In addition, the embryo can be tested for totipotency by implanting it into the uterus of an animal and allowing development to term.

Once a cloned totipotent embryo is produced from the methods described above for a non-bovine ungulate, the embryo can be further manipulated. Such manipulations include cryopreserving, thawing, culturing, disaggregating the embryo into single cells, and implanting the embryo. The embryo may be cultured in an artificial development environment (as described previously) or may be placed in utero of a properly synchronized female animal. An embryo derived from one specie may be placed in a uterus of the same or different specie. For example, a bison-derived embryo can be placed in the uterus of a bovine. The embryo can be allowed to develop until term, or may be retrieved from the uterine environment before birth.

Example 7

Multiple Pathways for Cloning Animals

Figure 3:
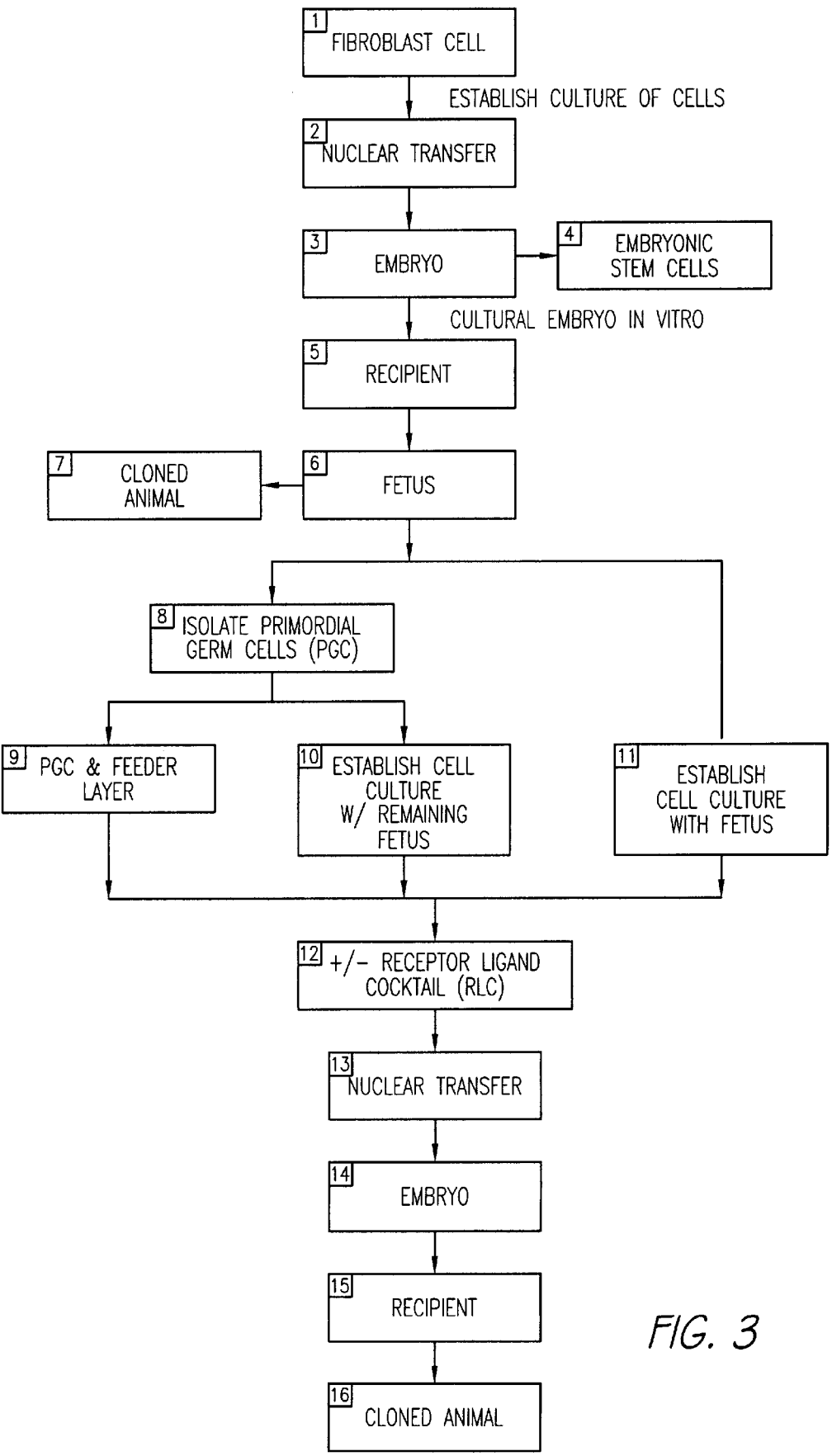
FIG. 3 illustrates multiple embodiments of the invention related to pathways for establishing totipotent cell lines and cloned animals. Fibroblast cells can be isolated from any source described herein. This figure is described in further detail in the Examples section.

FIG. 3 illustrates multiple embodiments of the invention. Animals can be cloned from cells that are reprogrammed into totipotent and immortalized cells.

Fibroblast cell cultures were prepared as defined above from ear punches extracted from an adult bovine animal. However, the cell cultures could be established from any type of differentiated cell. Individual cells isolated from these cultures were utilized as nuclear donors in a nuclear transfer process, labeled as step 2 in FIG. 3. Although one nuclear transfer cycle was utilized to obtain embryos (labeled as step 3 in FIG. 3), multiple nuclear transfer cycles could be applied to obtain these embryos. Also optional is (1) the addition of a stimulus before or after nuclear transfer, and (2) an activation step before or after nuclear transfer.

The embryo of step 3 in FIG. 3 was implanted into a recipient bovine female as described herein and a fetus (step 7) was isolated from that female. Cells isolated from embryos of step 3 may be utilized to establish embryonic stem cell cultures (step 4). In addition, the embryos of step 3 may be implanted into a female host and allowed to develop into a cloned animal (step 5).

The steps labelled 8, 9, 10, 1 1, and 12 in FIG. 3 were performed to establish totipotent and immortalized cells. The fetus of step 7 was manipulated in three manners. The manipulation in step 8 involved the isolation of genital ridge cells, specifically primordial germ cells, from the fetus of step 7. In step 9, the primordial germ cells were placed in co-culture with feeder cells. The feeder cells were either established from mouse fibroblast cells or from the rest of the fetus from which the primordial germ cells were extracted. Example 1 defines a method for establishing feeder cells. The head region and body cavity contents were removed from the fetus before the fetus was digested into a consistency suitable for establishing feeder cells. However, the fetus may be digested before the head region and contents of the body cavity are removed. In addition, feeder cells may be established from a fetus other than the fetus from which the primordial germ cells are isolated.

In step 10, a cell culture was established with a digested fetus from which the primordial germ cells, head region, and body cavity contents were removed. Step 11 illustrates that cell cultures may be established utilizing fetuses from which no cell types have been removed.

In step 12, cell cultures were either (1) subjected to a mechanical stimulus, or (2) not subjected to a mechanical stimulus. When applied, the mechanical stimulus was effected by supplementing the culture medium with a receptor ligand cocktail comprising 100 ng/ml human recombinant leukemia inhibitory factor (hrLIF; R&D System, Cat #250-L) and 100 ng/ml bovine basic fibroblast growth factor (bFGF; R&D System, Cat #133-FB). After step 12, cells were isolated from the cell cultures and utilized as nuclear donors in nuclear transfer processes, which are defined previously. Although one nuclear transfer cycle was utilized for step 13, more than one nuclear transfer cycle could be utilized.

Embryos developed after the nuclear transfer process of step 13. The embryos of step 14 may be implanted into a bovine recipient female and develop into a cloned bovine animal.

Cells isolated from any of the developing cell masses of steps 1, 3, 4, 5, 7, 8, 9, 10, 11, 12, 13, and 16 in FIG. 3 may be transfected with a DNA construct to form transgenic cells suitable for cloning transgenic animals. One embodiment for cloning transgenic animals is defined in the next example.

Example 8

Cloning Transgenic Animals

Figure 4:
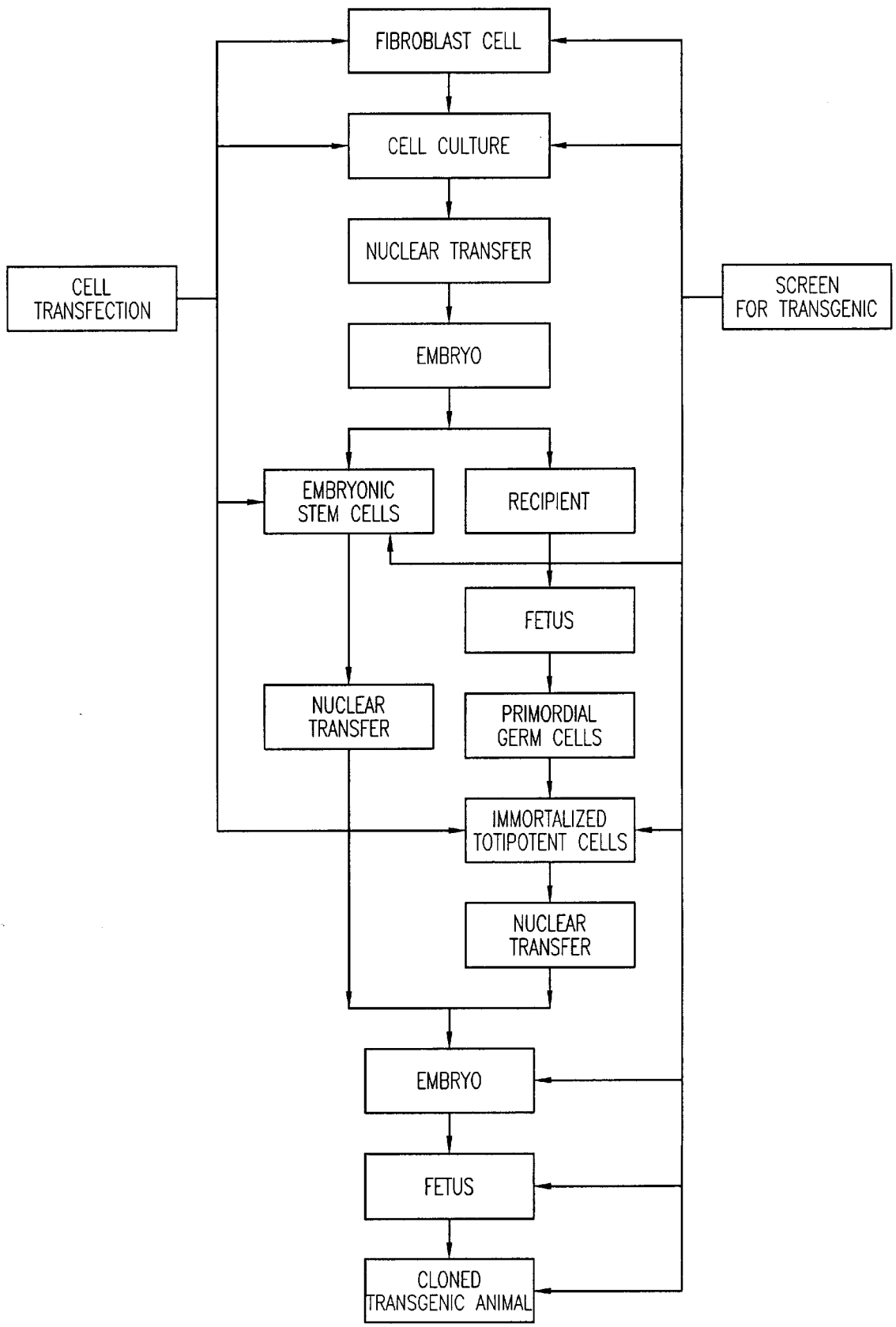
FIG. 4 illustrates multiple embodiments of the invention for creating cloned transgenic cell lines and cloned transgenic animals. This figure is described in further detail in the Examples section.

Transgenic cells suitable for creating a cloned transgenic animal can be prepared from cells isolated from an adult animal. FIG. 4 illustrates processes that can be utilized to create such transgenic cells. Although transgenic cells can be created from nearly any cell type by using the teachings of the invention, FIG. 4 illustrates procedures for establishing transgenic embryonic stem cells and transgenic immortalized and totipotent cells.

Fibroblast cell cultures can be established from ear punches extracted from a bovine animal as defined previously. Individual cells can be isolated from this cell culture and utilized as nuclear donors in a nuclear transfer process. A single nuclear transfer cycle or multiple nuclear transfer cycles can be applied. Other optional steps are defined in the previous example.

Pre-blastocyst stage embryos and/or blastocyst stage embryos developed from the nuclear transfer process can be utilized to establish embryonic stem cells. Materials and methods for preparing embryonic stem cells are described for transgenic modification by utilizing one or more screening techniques. Examples of these techniques are: (1) polymerase chain reaction, (2) Southern blotting, and (3) FISH-filter procedures. These techniques are well known to a person of ordinary skill in the art. The latter two techniques are utilized to determine the number of copies of an inserted gene sequence in embryonic stem cell nuclear DNA.

These screening procedures can be applied to transfected cells at any of the steps indicated in FIG. 4. Cloned transgenic animals may be created from transgenic fetuses. Table 4 shows the cloned bovine animals produced by the methods described in Examples 1–8.

TABLE 4

Development of Immortalized and Totipotent Cells Bovine Animals Produced

| Date of Birth | Gender | Breed | Age of Fetus Harvested (days) | Type of Cell Used (1° NT) | Type of Cell Used (2° NT) | Stimulus |
|---|---|---|---|---|---|---|
| 2/6/97 | M | H | 60 (est) | EG | Blastomere | LIF, FGF |
| 7/7/97 (*) | M | H | 60 (est) | EG | Blastomere | LIF, FGF |
| 7/7/97 (*) | M | H | 60 (est) | EG | Blastomere | LIF, FGF |
| 2/7/98 | F | H | 55 (est) | EG | Blastomere | LIF, FGF, FSK |
| 2/26/98 | F | H | 55 (est) | EG | Blastomere | LIF, FGF, FSK |
| 10/26/98 | F | H | 55 (est) | EG | Blastomere | LIF, FGF, FSK |
| 10/28/98 | F | H | 58 | EG | Blastomere | LIF, FGF, FSK |
| 12/2/98 | F | BS | 58 | EG | n/a | LIF, FGF, FSK |
| 12/6/98 | F | H | 58 | EG | n/a | Culture |
| 12/22/98 (*) | F | H | 58 | EG | n/a | Culture |
| 12/22/98 | F | H | 58 | EG | n/a | Culture |
| 12/22/98 (*) | F | H | 58 | EG (t) | n/a | LIF, FGF |
| 12/30/98 | F | H | 58 | EG | n/a | Culture |
| 12/30/98 | F | H | 58 | EG | n/a | Culture |
| 12/31/98 | F | H | 58 | EG | n/a | Culture |
| 1/6/99 | F | H | 58 | EG (t) | n/a | LIF, FGF |
| 1/7/99 | F | H | 58 | EG | n/a | Culture |
| 1/7/99 | F | H | 58 | EG | n/a | Culture |
| 1/15/99 | F | H | 58 | EG | n/a | Culture |
| 1/15/99 | F | H | 58 | EG (t) | n/a | LIF, FGF |
| 1/19/99 | F | H | 58 | EG (t) | n/a | LIF, FGF |

(*) - Stillborn
H - Holstein
BS - Brown Swiss
Age of fetus harvested - Age (in days) of fetus used as a source of precursor cells in 1° NT
(t) - transgenic nuclear donor: a nuclear donor cell transfected with a DNA construct having a human α glucosidase gene
EGF - Epidermal growth factor
LIF - Leukemia inhibitor factor
FSK - Forskolin by Stice et al., 1996, *Biology of Reproduction* 54: 100–110, hereby incorporated by reference herein in its entirety, including all figures, tables, and drawings. Immortalized and totipotent cells can be established according to the procedures defined in previous examples.

Cells can then be transfected with a DNA construct. Cells can be transfected at multiple steps, as indicated in FIG. 4. Materials and methods for preparing transgenic cells are defined in publications referenced previously. Immortalized and totipotent cells of the invention were successfully transfected with a DNA construct comprising (a) a neomycin gene, which encodes a product that renders cells resistant to a compound designated G418; (b) a gene encoding the enzyme α-glucosidase; and (c) a casein promoter element. The transfected cells were selected for transgenic modification by selecting for transgenic cells in cell culture conditions harboring G418. The transgenic cells are then screened While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

Other embodiments are set forth within the following claims.

What is claimed is:

1. A method of cloning a bovine, said method comprising:
   a) obtaining a cell from a bovine fetus of not less than about 35 days of gestation and not more than about 70 days of gestation;
   b) reprogramming said cell by incubating said cell in a medium comprising LIF and FGF to form a reprogrammed cell;
   c) forming a cybrid by nuclear transfer of said reprogrammed cell into an enucleated bovine oocyte; and
   d) culturing said cybrid so as to generate an embryo comprising embryonic cells; and
   e) transferring said embryo of step (d) or a recloned embryo of said embryo of step (d) into the uterus of a host bovine so as to produce a fetus which undergoes full fetal development and parturition; whereby a viable clone of said bovine is generated.

2. The method of claim 1 wherein the embryo of step (d) is recloned one or more times.

3. The method of claim 1, further comprising introducing a heterologous DNA sequence into said cell to produce a transgenic cell.

4. The method of claim 1, wherein the bovine fetus of step (a) is produced by in vivo or in vitro fertilization of a bovine oocyte.

5. The method of claim 1, wherein after culturing, said embryo is cryopreserved, whereby storage, transportation, and later transfer into said host bovine may be achieved.

6. The method of claim 5, wherein said cryopreserved embryo is thawed and transferred into said host bovine, optionally further culturing said embryo after thawing and prior to transfer.

7. The method of claim 1, wherein said enucleated bovine oocyte of step (c) is an enucleated young bovine oocyte.

8. The method of claim 7, wherein said young bovine oocyte is incubated for about 16 to 28 hours to form a first polar body prior to enucleation.

9. The method of claim 1, wherein said enucleated bovine oocyte of step (c) is an enucleated aged bovine oocyte.

10. The method of claim 1, wherein said bovine is an individual of a species selected from the group consisting of *Bos taurus, Bos indicus,* or *Bos buffaloes.*

11. The method of claim 1, wherein said reprogrammed cell has the properties of an embryonic germ cell.

12. The method of claim 1, wherein said cell of step (a) is a genital ridge cell.

13. The method of claim 12, wherein said genital ridge cell is disaggregated from a genital ridge using a proteolytic enzyme.

14. The method of claim 1, wherein said recloned embryo is established by a process comprising the steps of:
   i) removing a blastomere from said embryo of step (d);
   ii) fusing said blastomere with a recipient bovine oocyte to form a second cybrid; and
   iii) culturing said second cybrid to establish said recloned embryo.

15. The method of claim 14, wherein said recloned embryo is cultured for a period of time and then is transplanted into the uterus of a host bovine, whereby pregnancy and live birth of a calf having the same genetic makeup as the bovine embryo from which the blastomere was obtained is achieved.

16. The method of claim 15, wherein said period of time is about 4 to 10 days.

17. The method of claim 15, wherein said period of time is 6 to 7 days.

18. The method of claim 14, wherein said blastomere is removed from an embryo at the morula stage.

19. The method of claim 14, wherein said recipient bovine oocyte is an enucleated aged bovine oocyte.

20. The method of claim 19, wherein said aged bovine oocyte is incubated in culture for about 28 to 48 hours prior to enucleation.

21. A method of producing a totipotent bovine cell line comprising:
   a) obtaining non-embryonic bovine cells;
   b) reprogramming said cells by incubating said cells in a medium comprising LIF and FGF to form reprogrammed cells; and
   c) culturing said reprogrammed cells as a totipotent cell line.

22. A method of producing a totipotent bovine cell line comprising:
   a) obtaining non-embryonic bovine cells;
   b) reprogramming said cells by incubating said cells in a medium comprising LIE and FGF to form reprogranmed cells;
   c) fusing a said reprogrammed cell with an enucleated young oocyte by performing a nuclear transfer to form a cybrid;
   d) culturing said cybrid so as to generate an embryo comprising embryonic cells; and
   e) culturing said embryonic cells to generate a totipotent cell line.

23. The method of claim 21 or 22, wherein the bovine cells are obtained from a bovine species selected from the group consisting of *Bos taurus, Bos indicus*, and *Bos buffaloes*.

24. The method of claim 21 or 22, wherein said reprogrammed cells have the properties of embryonic germ cells.

25. The method of claim 21 or 22, wherein said non-embryonic bovine cells are genital ridge cells.

26. A method for cloning a bovine, comprising the steps of:

a) obtaining a non-embryonic bovine cell;

b) reprogramming said non-embryonic bovine cell cells by incubating said cell in a medium comprising LIF and FGF to form a reprogrammed cell, wherein said reprogrammed cell is immortalized and totipotent;

c) forming a cybrid by nuclear transfer of said reprogrammed cell into an enucleated bovine oocyte; and d) culturing said cybrid so as to generate an embryo comprising embryonic cells; and e) transferring said embryo of step (d) or a recloned embryo of said embryo of step (d) into the uterus of a host bovine for developing said bovine.

27. The method of claim 1, 21, 22, or 26, wherein said LIF is selected from the group consisting of human LIF and bovine LIF.

28. The method of claim 26, wherein said reprogrammed cell has the properties of an embryonic germ cell.

29. The method of claim 26, wherein said non-embryonic bovine cell is a genital ridge cell.

\* \* \* \* \*